United States Patent
Jeong et al.

(10) Patent No.: US 10,564,320 B2
(45) Date of Patent: Feb. 18, 2020

(54) COMPOUND, PHOTOSENSITIVE RESIN COMPOSITION INCLUDING THE SAME, AND COLOR FILTER

(71) Applicant: SAMSUNG SDI CO., LTD., Yongin-si (KR)

(72) Inventors: Euisoo Jeong, Suwon-si (KR); Hyewon Seo, Suwon-si (KR); Myoungyoup Shin, Suwon-si (KR); Sunwoong Shin, Suwon-si (KR); Juho Jung, Suwon-si (KR); Gyuseok Han, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 68 days.

(21) Appl. No.: 15/837,328

(22) Filed: Dec. 11, 2017

(65) Prior Publication Data

US 2018/0335547 A1    Nov. 22, 2018

(30) Foreign Application Priority Data

May 17, 2017    (KR) .................. 10-2017-0061181

(51) Int. Cl.
| | | |
|---|---|---|
| G02B 5/20 | (2006.01) | |
| C09B 47/04 | (2006.01) | |
| G03F 7/004 | (2006.01) | |
| G02B 1/04 | (2006.01) | |
| C07F 3/06 | (2006.01) | |
| G03F 7/00 | (2006.01) | |
| G03F 7/033 | (2006.01) | |
| G03F 7/031 | (2006.01) | |
| G02B 5/22 | (2006.01) | |
| C09B 47/06 | (2006.01) | |
| G02F 1/1335 | (2006.01) | |

(52) U.S. Cl.
CPC .................. *G02B 1/04* (2013.01); *C07F 3/06* (2013.01); *C09B 47/04* (2013.01); *C09B 47/061* (2013.01); *G02B 5/223* (2013.01); *G03F 7/0007* (2013.01); *G03F 7/0045* (2013.01); *G03F 7/031* (2013.01); *G03F 7/033* (2013.01); *G02F 1/133514* (2013.01); *G02F 1/133516* (2013.01); *G02F 2202/022* (2013.01)

(58) Field of Classification Search
CPC ..... C09B 47/04; C09B 47/061; G03F 7/0007; G02B 5/20; G02B 5/223
USPC ............................................................ 430/7
See application file for complete search history.

(56) References Cited

U.S. PATENT DOCUMENTS

| 9,080,055 | B2 | 7/2015 | Braun et al. |
| 9,815,843 | B2 | 11/2017 | Pak et al. |
| 2017/0107224 | A1 | 4/2017 | Pak et al. |

FOREIGN PATENT DOCUMENTS

| CN | 103323897 A | | 9/2013 |
| CN | 105085535 A | | 11/2015 |
| EP | 1996549 A1 | | 12/2008 |
| JP | 06-041458 | | 2/1994 |
| JP | H-07140654 A | | 6/1995 |
| JP | H-10254133 A | | 9/1998 |
| JP | 2008050599 A | | 3/2008 |
| JP | 2010-251241 A | | 11/2010 |
| JP | 2013213208 A | | 10/2013 |
| JP | 2014015542 A | | 1/2014 |
| JP | 2014-028950 | * | 2/2014 |
| JP | 2014508822 | | 4/2014 |
| JP | 2015040214 A | | 3/2015 |
| JP | 5865341 B2 | | 2/2016 |
| JP | 2016-124888 | * | 7/2016 |
| JP | 2016-124888 A | | 7/2016 |
| KR | 1999-0007097 A | | 1/1999 |
| KR | 2002-0015650 A | | 2/2002 |
| KR | 2005-0020653 A | | 3/2005 |
| KR | 2009-0106226 A | | 10/2009 |

(Continued)

OTHER PUBLICATIONS

Computer-generated translation of JP 2014-028950 (Feb. 2014). (Year: 2014).*

(Continued)

*Primary Examiner* — John A McPherson
(74) *Attorney, Agent, or Firm* — Lee & Morse, P.C.

(57) ABSTRACT

A compound represented by Chemical Formula 1, a photosensitive resin composition including the same, and a color filter manufactured using the photosensitive resin composition are provided.

[Chemical Formula 1]

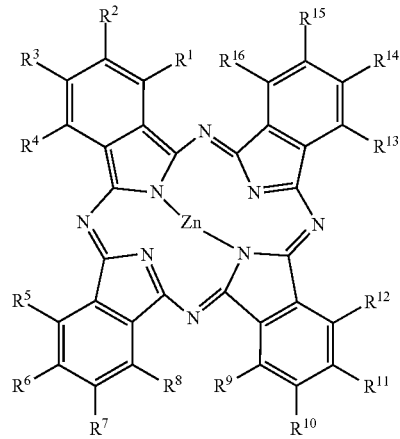

In Chemical Formula 1, each substituent is the same as defined in the specification.

17 Claims, No Drawings

(56) References Cited

FOREIGN PATENT DOCUMENTS

| | | | |
|---|---|---|---|
| KR | 2010-0078845 A | 7/2010 | |
| KR | 2010-0080142 A | 7/2010 | |
| KR | 101336306 B1 | 12/2013 | |
| KR | 101478296 B1 | 12/2014 | |
| KR | 2016-0007024 A | 1/2016 | |

OTHER PUBLICATIONS

Computer-generated translation of JP 2016-124888 (Jul. 2016). (Year: 2016).*

Shaya Y. Al-Raqa, "The synthesis and photophysical properties of novel, symmetrical, hexadecasubstituted Zn phthalocyanines and related unsymmetrical derivatives", Dyes and Pigments, vol. 77, pp. 259-265.

Saad Makhseed, et al., "The synthesis and characterization of zincphthalocyanines bearing functionalized bulky phenoxy substituents", Dyes and Pigments, vol. 82, pp. 1-5.

Saad Makhseed, et al., "New highly soluble phenoxy-substituted phthalocyanine and azaphthalocyanine derivatives: Synthesis, photochemical and photophysical studies and atypical aggregation behavior", Dyes and Pigments, vol. 95, pp. 351-357.

Shaya Y. Al-Raqa, et al., "Preparation and optical properties of novel symmetrical hexadecachlorinatedpht halocyaninato zinc(II) spin coated thin films", Polyhedron, vol. 27, pp. 1256-1261.

Ibrahim Ozcesmeci, "Synthesis and fluorescence properties of phthalocyanines with dibromo- and tribromo-phenoxy functionalities", Synthetic Metals, vol. 176, pp. 128-133.

Tasaltin, et al., "Synthesis and DMP sensing properties of fluoroalkyloxy and fluoroaryloxy substituted phthalocyanines in acoustic sensors", Sensors and Actuators B: Chemical, vol. 150, pp. 781-787.

Taiwanese Office Action dated Jan. 30, 2019.

Chinese Office Action dated Feb. 11, 2019.

\* cited by examiner

COMPOUND, PHOTOSENSITIVE RESIN COMPOSITION INCLUDING THE SAME, AND COLOR FILTER

CROSS-REFERENCE TO RELATED APPLICATION

Korean Patent Application No. 10-2017-0061181, filed on May 17, 2017, in the Korean Intellectual Property Office, and entitled: "Novel Compound, Photosensitive Resin Composition Comprising the Same and Color Filter," is incorporated by reference herein in its entirety.

BACKGROUND

1. Field

Embodiments relate to a compound, a photosensitive resin composition including the same, and a color filter.

2. Description of the Related Art

A liquid crystal display device among many kinds of displays has an advantage of lightness, thinness, low cost, low power consumption for operation, and improved adherence to an integrated circuit, and has been widely used for a laptop computer, a monitor, and a TV screen.

SUMMARY

Embodiments are directed to a compound represented by Chemical Formula 1:

[Chemical Formula 1]

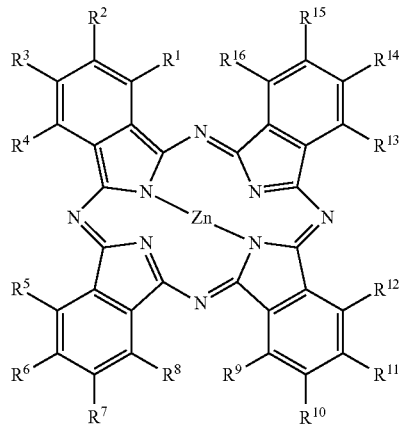

In Chemical Formula 1, $R^1$ to $R^{16}$ may each independently be a hydrogen atom, a halogen atom, a substituted or unsubstituted C1 to C20 alkyl group, a substituted or unsubstituted C3 to C20 alkoxy group, a substituted or unsubstituted C6 to C20 aryl group, or a substituted or unsubstituted C6 to C20 aryloxy group. One or more of $R^1$ to $R^{16}$ may be represented by Chemical Formula 2,

[Chemical Formula 2]

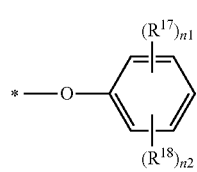

In Chemical Formula 2, $R^{17}$ and $R^{18}$ may each independently be a halogen atom, and n1 and n2 may each independently be an integer ranging from 0 to 5, and n1 and n2 may satisfy $1 \leq n1+n2 \leq 5$.

Chemical Formula 2 may be represented by one selected from Chemical Formula 3-1 to Chemical Formula 3-4:

[Chemical Formula 3-1]

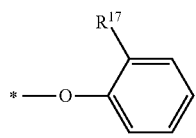

[Chemical Formula 3-2]

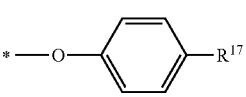

[Chemical Formula 3-3]

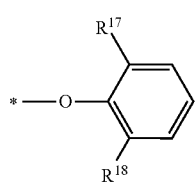

[Chemical Formula 3-4]

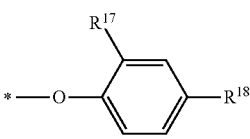

In Chemical Formulae 3-1 to 3-4, $R^{17}$ and $R^{18}$ may each independently be a halogen atom.

At least one of $R^1$ to $R^{16}$ may be represented by Chemical Formula 2 and at least one of $R^1$ to $R^{16}$ may be represented by Chemical Formula 4:

[Chemical Formula 4]

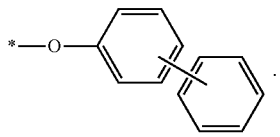

At least one of $R^1$ to $R^{16}$ may be represented by Chemical Formula 2, at least one of $R^5$ to $R^8$ may be represented by Chemical Formula 4, at least one of $R^9$ to $R^{12}$ may be represented by Chemical Formula 4, and at least one of $R^{13}$ to $R^{16}$ may be represented by Chemical Formula 4.

At least one of $R^1$ to $R^4$ may be represented by Chemical Formula 2, at least one of $R^5$ to $R^8$ may be represented by Chemical Formula 2, at least one of $R^9$ to $R^{12}$ may be represented by Chemical Formula 4, and at least one of the $R^{13}$ to $R^{16}$ may be represented by Chemical Formula 4.

At least one of $R^1$ to $R^4$ may be represented by Chemical Formula 2, at least one of $R^5$ to $R^8$ may be represented by Chemical Formula 4, at least one of $R^9$ to $R^{12}$ may be represented by Chemical Formula 2, and at least one of $R^{13}$ to $R^{16}$ may be represented by Chemical Formula 4.

At least one of $R^1$ to $R^4$ may be represented by Chemical Formula 2, at least one of $R^5$ to $R^8$ may be represented by Chemical Formula 2, at least one of $R^9$ to $R^{12}$ may be represented by Chemical Formula 2, and at least one of $R^{13}$ to $R^{16}$ may be represented by Chemical Formula 4.

At least one of $R^1$ to $R^4$ may be represented by Chemical Formula 2, at least one of $R^5$ to $R^8$ may be represented by Chemical Formula 2, at least one of $R^9$ to $R^{12}$ may be represented by Chemical Formula 2, and at least one of $R^{13}$ to $R^{16}$ may be represented by Chemical Formula 2.

The compound represented by Chemical Formula 1 may be represented by one of Chemical Formula 5 to Chemical Formula 14:

[Chemical Formula 5]

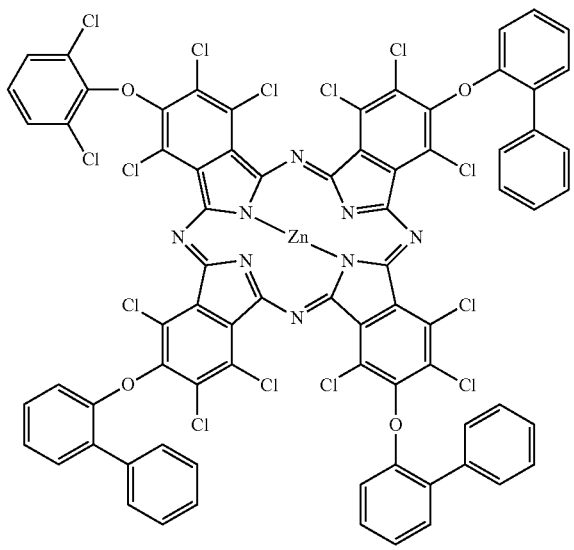

[Chemical Formula 6]

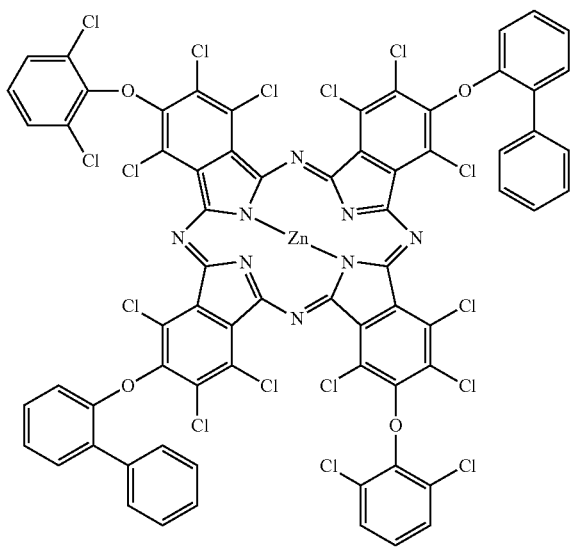

[Chemical Formula 7]

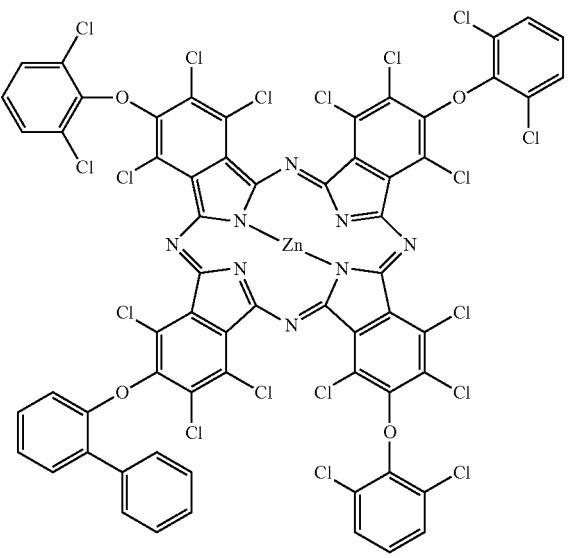

[Chemical Formula 8]

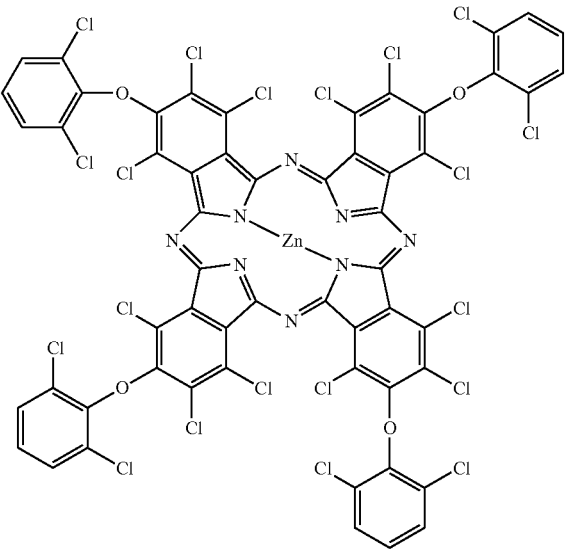

[Chemical Formula 9]
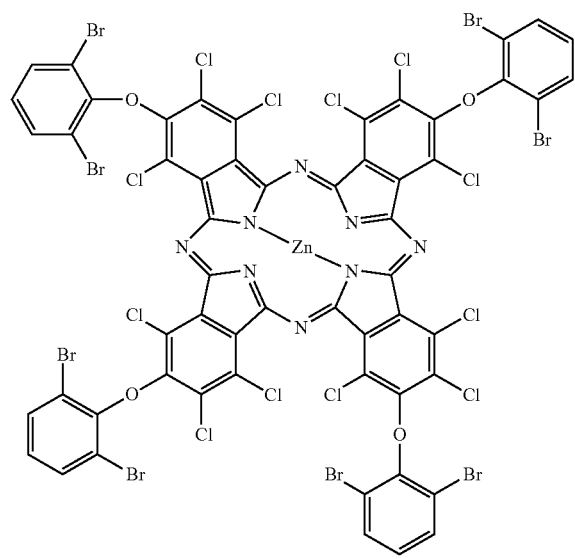
[Chemical Formula 10]
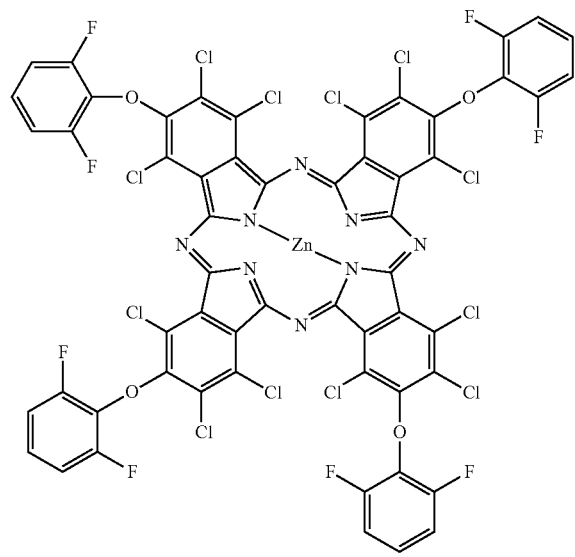
[Chemical Formula 11]
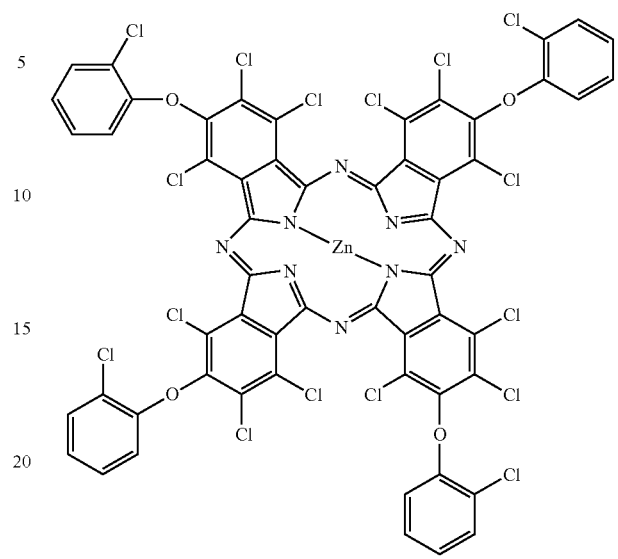
[Chemical Formula 12]
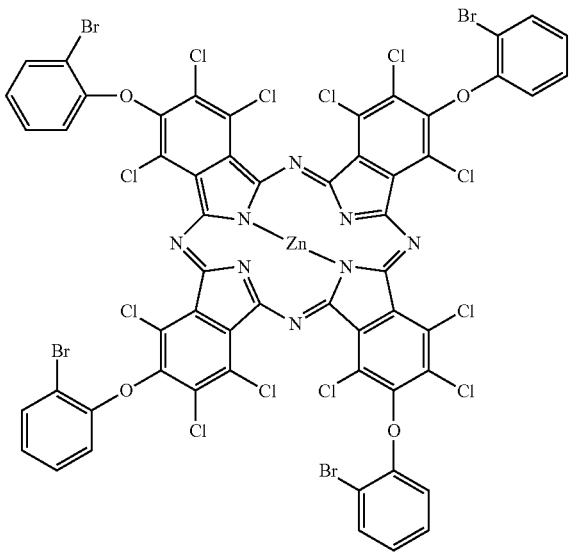

[Chemical Formula 13]

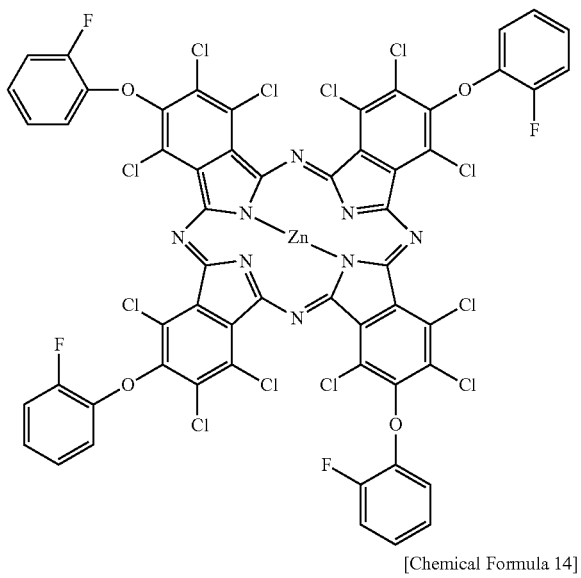

[Chemical Formula 14]

The compound may be a green dye.

The green dye may have a maximum transmittance in a 445 nm to 560 nm wavelength range.

Embodiments are also directed to a photosensitive resin composition including the compound according to an embodiment.

The photosensitive resin composition may include about 1 wt % to about 10 wt % of the compound based on a total amount of the photosensitive resin composition.

The photosensitive resin composition may further include a binder resin, a photopolymerizable compound, a photopolymerization initiator, and a solvent.

The photosensitive resin composition may further include a pigment.

The pigment may include a yellow pigment, a green pigment, or a combination thereof.

Embodiments are also directed to a color filter manufactured using the photosensitive resin composition according to an embodiment.

Embodiments are also directed to a color filter including the compound according to an embodiment.

Embodiments are also directed to an electronic device comprising a display having a color filter, the color filter including the compound according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. In the drawing figures, the dimensions of layers and regions may be exaggerated for clarity of illustration. Like reference numerals refer to like elements throughout.

As used herein, when specific definition is not otherwise provided, the term "substituted" refers to one substituted with a substituent selected from a halogen (F, Br, Cl, or I), a hydroxy group, a nitro group, a cyano group, an amino group ($NH_2$, $NH(R^{200})$ or $N(R^{201})(R^{202})$ wherein $R^{200}$, $R^{201}$, and $R^{202}$ are the same or different, and are independently a C1 to C10 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group, and a substituted or unsubstituted heterocyclic group.

As used herein, when specific definition is not otherwise provided, the term "alkyl group" refers to a C1 to C20 alkyl group, and specifically a C1 to C15 alkyl group, the term "cycloalkyl group" refers to a C3 to C20 cycloalkyl group, and specifically a C3 to C18 cycloalkyl group, the term "alkoxy group" refers to a C1 to C20 alkoxy group, and specifically a C1 to C18 alkoxy group, the term "aryl group" refers to a C6 to C20 aryl group, and specifically a C6 to C18 aryl group, the term "alkenyl group" refers to a C2 to C20 alkenyl group, and specifically a C2 to C18 alkenyl group, the term "alkylene group" refers to a C1 to C20 alkylene group, and specifically C1 to C18 alkylene group, and the term "arylene group" refers to a C6 to C20 arylene group, and specifically a C6 to C16 arylene group.

As used herein, when specific definition is not otherwise provided, "(meth)acrylate" refers to "acrylate" and "methacrylate" and "(meth)acrylic acid" refers to "acrylic acid" and "methacrylic acid."

As used herein, when a definition is not otherwise provided, the term "combination" refers to mixing or copolymerization. In addition, "copolymerization" refers to block copolymerization and to random copolymerization, and "copolymer" refers to a block copolymer and to a random copolymer.

In the chemical formula of the present specification, unless a specific definition is otherwise provided, hydrogen is bonded at the position when a chemical bond is not drawn where supposed to be given.

As used herein, when specific definition is not otherwise provided, "*" indicates a point where the same or different atom or chemical formula is linked.

An example embodiment provides a compound represented by Chemical Formula 1.

[Chemical Formula 1]

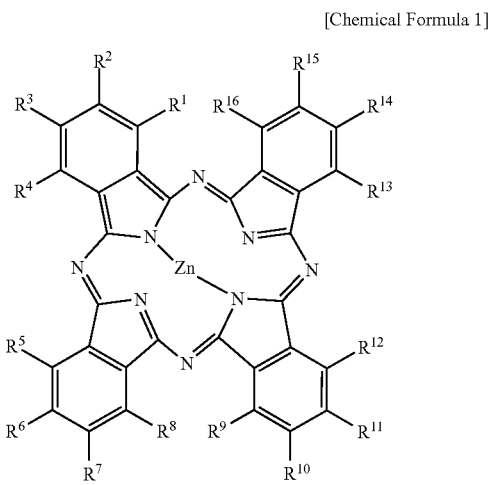

In Chemical Formula 1, $R^1$ to $R^{16}$ may independently be a hydrogen atom, a halogen atom, a substituted or unsubstituted C1 to C20 alkyl group, a substituted or unsubstituted C3 to C20 alkoxy group, a substituted or unsubstituted C6 to C20 aryl group, or a substituted or unsubstituted C6 to C20 aryloxy group.

In an example embodiment, at least one of $R^1$ to $R^{16}$ may be represented by Chemical Formula 2,

[Chemical Formula 2]

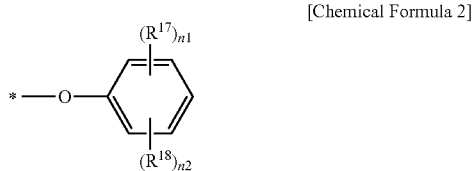

In Chemical Formula 2, $R^{17}$ and $R^{18}$ are independently a halogen atom, and n1 and n2 may independently be an integer ranging from 0 to 5. In an example embodiment, $1 \le n1+n2 \le 5$.

The compound represented by Chemical Formula 1 may provide excellent green spectral characteristics and a high molar extinction coefficient. Furthermore, the compound represented by Chemical Formula 1 including the substituent represented by Chemical Formula 2 may provide excellent solubility in an organic solvent and excellent luminance and contrast ratio during application to a color filter.

Chemical Formula 2 may be represented by, for example, one selected from Chemical Formula 3-1 to Chemical Formula 3-4.

[Chemical Formula 3-1]

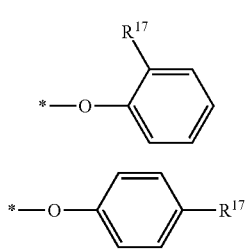

[Chemical Formula 3-2]

[Chemical Formula 3-3]

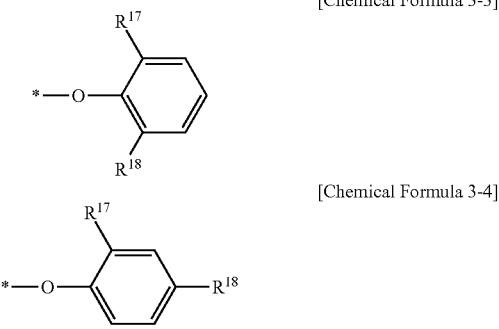

[Chemical Formula 3-4]

In Chemical Formula 3-1 to Chemical Formula 3-4, $R^{17}$ and $R^{18}$ are independently a halogen atom.

The substituents represented by Chemical Formulae 3-1 to 3-4 may be, for example, aryloxy groups substituted with at least one halogen atom. When at least one halogen atom is substituted in an ortho and/or para position, luminance and contrast ratio may be further improved. In addition, when the halogen atoms are all substituted in the ortho and para positions (for example, in the case that two halogen atoms are substituted), luminance and a contrast ratio may be more improved than when the halogen atom is substituted only in either ortho or para position (that is, when one halogen atom is substituted). Meta-substitution of the halogen atom (even if another halogen atom is also substituted in the ortho and/or para position), may provide lesser effects at improving luminance and a contrast ratio.

In further detail, in the substituent represented by Chemical Formula 2, for example, in the substituents represented by Chemical Formulae 3-1 to 3-4, the luminance and the contrast ratio may be further improved in the following order (i→ii→iii); i) at least one halogen atom is substituted is the meta position, ii) the halogen atom is substituted in either ortho or para position, and iii) the halogen is substituted in both of the ortho and para positions.

In an example embodiment, at least one of $R^1$ to $R^{16}$ may be represented by Chemical Formula 2 and at least one of $R^1$ to $R^{16}$ may be represented by Chemical Formula 4.

[Chemical Formula 4]

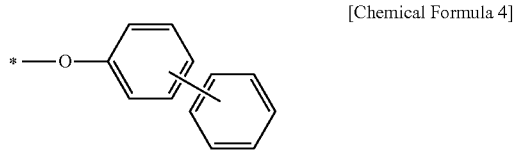

For example, the substituent represented by Chemical Formula 4 may be represented by Chemical Formula 4-1.

[Chemical Formula 4-1]

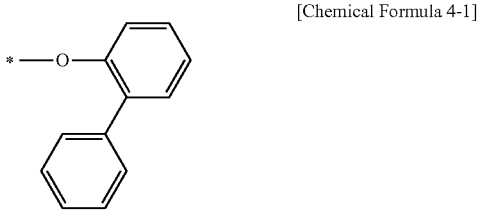

In an example embodiment, at least one of $R^1$ to $R^4$ may be represented by Chemical Formula 2, at least one of $R^5$ to $R^8$ may be represented by Chemical Formula 4, at least one of $R^9$ to $R^{12}$ may be represented by Chemical Formula 4, and at least one of the $R^{13}$ to $R^{16}$ may be represented by Chemical Formula 4.

For example, $R^2$ or $R^3$ may be represented by Chemical Formula 2, $R^6$ or $R^7$ may be represented by Chemical Formula 4, $R^{10}$ or $R^{11}$ may be represented by Chemical Formula 4, and $R^{14}$ or $R^{15}$ may be represented by Chemical Formula 4.

For example, $R^2$ or $R^3$ may be represented by Chemical Formula 2, $R^6$ or $R^7$ may be represented by Chemical Formula 4, $R^{10}$ or $R^{11}$ may be represented by Chemical Formula 4, $R^{14}$ or $R^{15}$ may be represented by Chemical Formula 4, and the remainders that are not represented by Chemical Formula 2 and Chemical Formula 4 may be all halogen atoms.

In an example embodiment, at least one of $R^1$ to $R^4$ may be represented by Chemical Formula 2, at least one of $R^5$ to $R^8$ may be represented by Chemical Formula 2, at least one of $R^9$ to $R^{12}$ may be represented by Chemical Formula 4, and at least one of $R^{13}$ to $R^{16}$ may be represented by Chemical Formula 4.

For example, $R^2$ or $R^3$ may be represented by Chemical Formula 2, $R^6$ or $R^7$ may be represented by Chemical Formula 2, $R^{10}$ or $R^{11}$ may be represented by Chemical Formula 4, and $R^{14}$ or $R^{15}$ may be represented by Chemical Formula 4.

For example, $R^2$ or $R^3$ may be represented by Chemical Formula 2, $R^6$ or $R^7$ may be represented by Chemical Formula 2, $R^{10}$ or $R^{11}$ may be represented by Chemical Formula 4, $R^{14}$ or $R^{15}$ may be represented by Chemical Formula 4, and the remainders that are not represented by Chemical Formula 2 and Chemical Formula 4 may be all halogen atoms.

In an example embodiment, at least one of $R^1$ to $R^4$ may be represented by Chemical Formula 2, at least one of $R^5$ to $R^8$ may be represented by Chemical Formula 4, at least one of $R^9$ to $R^{12}$ may be represented by Chemical Formula 2, and at least one of $R^{13}$ to $R^{16}$ may be represented by Chemical Formula 4.

For example, $R^2$ or $R^3$ may be represented by Chemical Formula 2, $R^6$ or $R^7$ may be represented by Chemical Formula 4, $R^{10}$ or $R^{11}$ may be represented by Chemical Formula 2, and $R^{14}$ or $R^{15}$ may be represented by Chemical Formula 4.

For example, $R^2$ or $R^3$ may be represented by Chemical Formula 2, $R^6$ or $R^7$ may be represented by Chemical Formula 4, $R^{10}$ or $R^{11}$ may be represented by Chemical Formula 2, $R^{14}$ or $R^{15}$ may be represented by Chemical Formula 4, and the remainders that are not represented by Chemical Formula 2 and Chemical Formula 4 may be all halogen atoms.

In an example embodiment, at least one of $R^1$ to $R^4$ may be represented by Chemical Formula 2, at least one of $R^5$ to $R^8$ may be represented by Chemical Formula 2, at least one of $R^9$ to $R^{12}$ may be represented by Chemical Formula 2, and at least one of $R^{13}$ to $R^{16}$ may be represented by Chemical Formula 2.

For example, $R^2$ or $R^3$ may be represented by Chemical Formula 2, $R^6$ or $R^7$ may be represented by Chemical Formula 2, $R^{10}$ or $R^{11}$ may be represented by Chemical Formula 2, and $R^{14}$ or $R^{15}$ may be represented by Chemical Formula 2.

For example, $R^2$ or $R^3$ may be represented by Chemical Formula 2, $R^6$ or $R^7$ may be represented by Chemical Formula 2, $R^{10}$ or $R^{11}$ may be represented by Chemical Formula 2, $R^{14}$ or $R^{15}$ may be represented by Chemical Formula 2, and the remainders that are not represented by Chemical Formula 2 may be all halogen atoms.

In an example embodiment, the compound represented by Chemical Formula 1 may be represented by one of Chemical Formula 5 to Chemical Formula 14, but is not limited thereto.

[Chemical Formula 5]

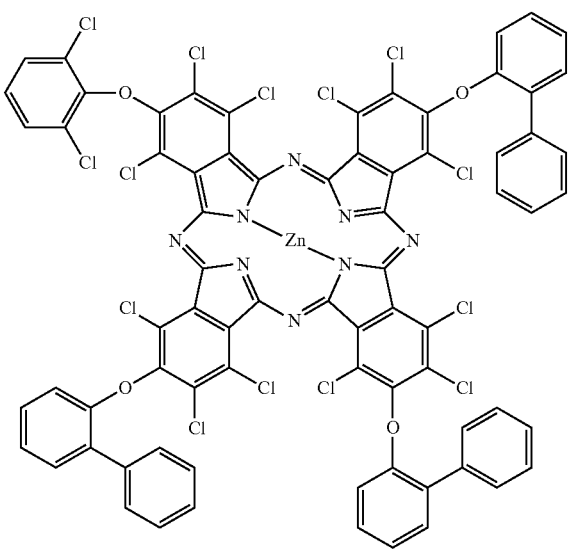

[Chemical Formula 6]
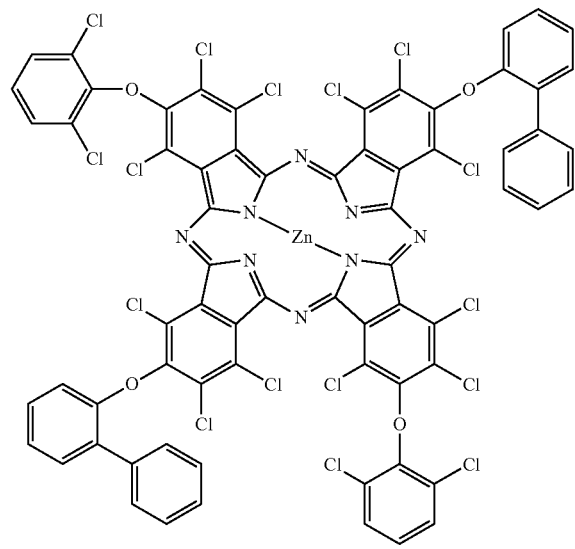
[Chemical Formula 7]
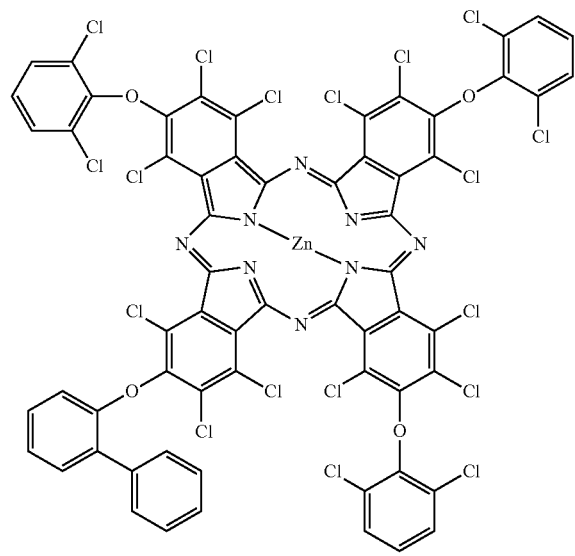
[Chemical Formula 8]
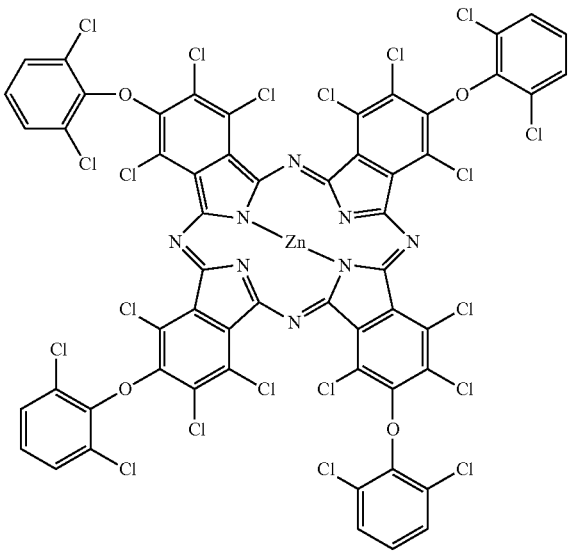
[Chemical Formula 9]
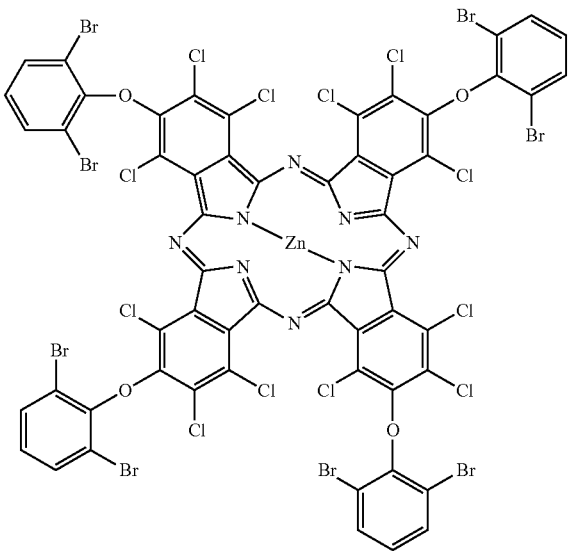

[Chemical Formula 10]
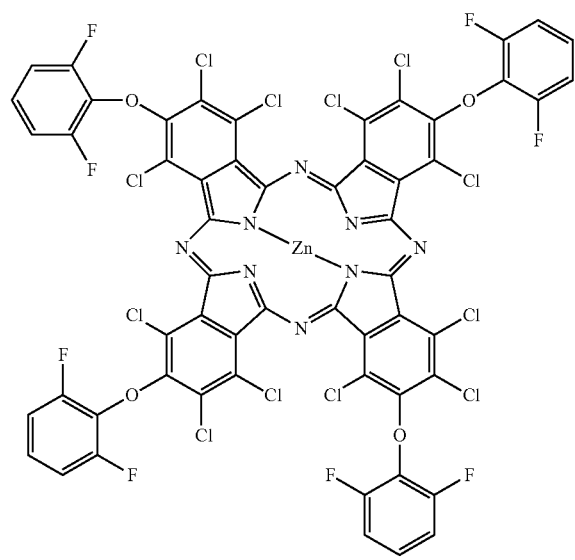
[Chemical Formula 12]
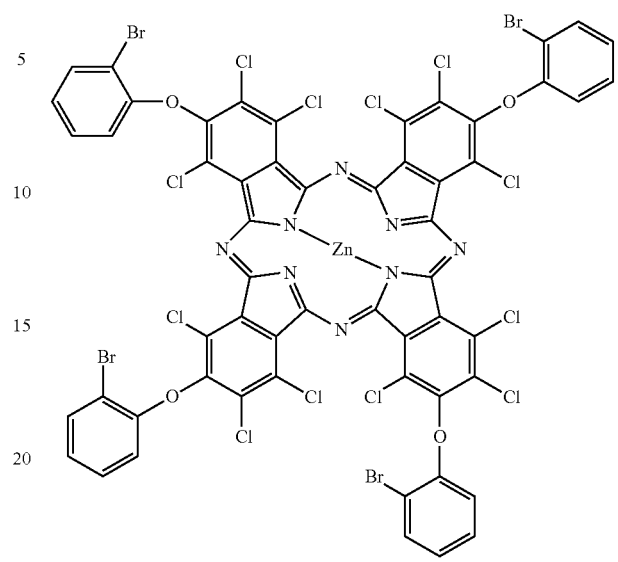
[Chemical Formula 11]
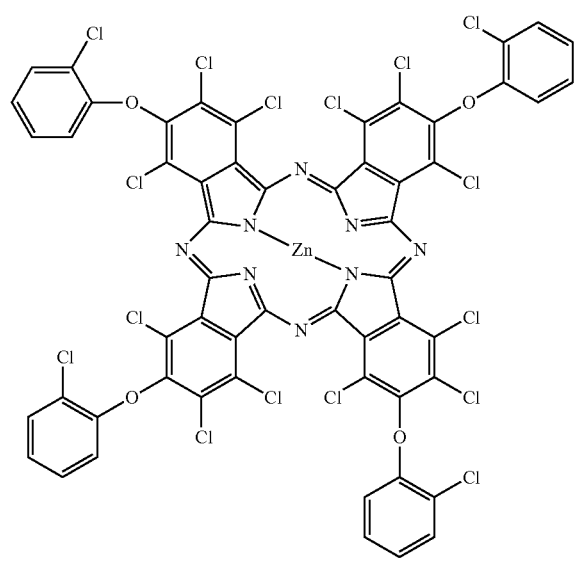
[Chemical Formula 13]
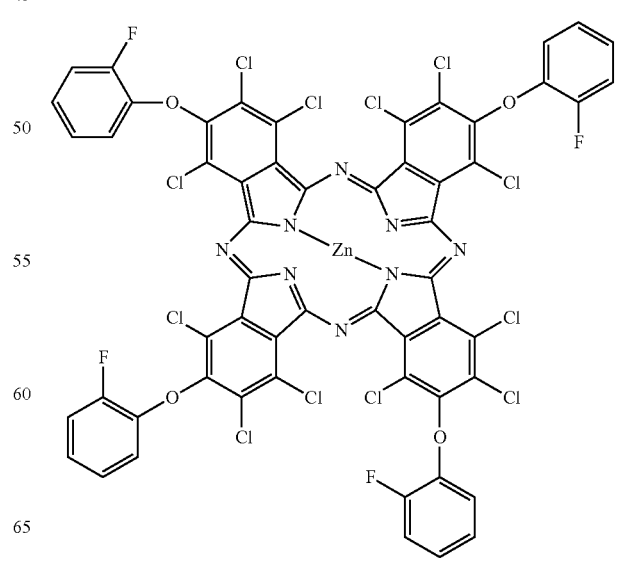

-continued

[Chemical Formula 14]

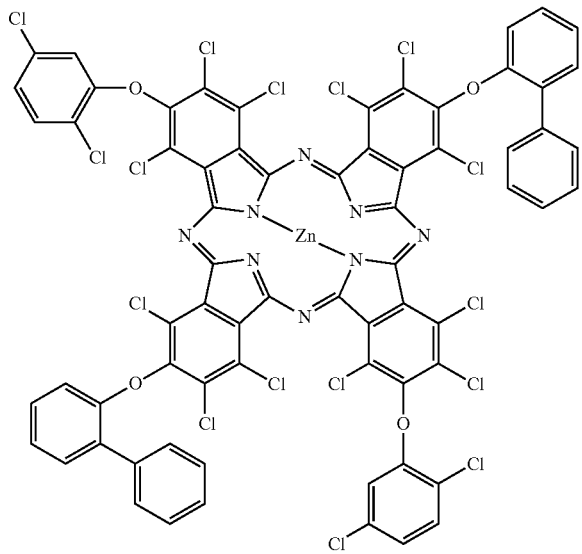

The compound according to an embodiment may express a clear color even in a small amount and, when the compound is used as a colorant, a display device having excellent color characteristics such as luminance, a contrast ratio, and the like may be manufactured by including the substituent represented by Chemical Formula 2, for example one of Chemical Formula 3-1 to Chemical Formula 3-4. For example, the compound may be a colorant, for example a dye, for example a green dye, for example a dye having maximum transmittance in a 445 nm to 560 nm wavelength range. In addition, the green dye may be a dye having maximum absorbance in 600 nm to 730 nm wavelength range.

In general, a dye is the most expensive among the components used in a color filter. If an expensive dye is used more to accomplish a desired effect, for example, high luminance, a high contrast ratio or the like, then this may increase the unit cost of production. However, when the compound according to an embodiment is used as a colorant, for example a dye in a color filter, the compound and/or the polymer may accomplish improved color characteristics such as high luminance or a high contrast ratio even though used in a small amount, which may thus reduce the unit cost of production.

According to another example embodiment, a photosensitive resin composition includes the compound according to an embodiment.

For example, the photosensitive resin composition may include a colorant including a compound according to the embodiment, a binder resin, a photopolymerizable compound, a photopolymerization initiator, and a solvent.

Hereinafter each component is specifically described.

Colorant

The colorant may include the compound according to the embodiment.

The colorant may further include, for example, a green pigment and/or a yellow pigment.

For example, the colorant may include the compound represented by Chemical Formula 1, a green pigment dispersion liquid, and a yellow pigment dispersion liquid. The compound represented by Chemical Formula 1 may include the substituent represented by Chemical Formula 2.

According to an example embodiment, the green dye may have a maximum transmittance in a 445 nm to 560 nm wavelength range, and a maximum absorbance in 600 nm to 730 nm wavelength range, which may help realize high color coordinates, and when the green dye is used as a colorant together with the green pigment dispersion liquid and the yellow pigment dispersion liquid, coloring properties, luminance, and a contrast ratio may be improved.

The colorant may include, for example, the compound represented by Chemical Formula 1, the green pigment dispersion liquid, and the yellow pigment dispersion liquid in each amount of 1 wt % to 10 wt % (for example, 3 wt % to 7 wt %), 60 wt % to 70 wt %, and 20 wt % to 30 wt % based on a total amount of the colorant. When the compound represented by Chemical Formula 1, the green pigment dispersion liquid, and the yellow pigment dispersion liquid are included in the colorant within the amount ranges, a colorant having improved coloring properties may be realized and a color filter having improved luminance and contrast ratio may be also realized.

For example, a green pigment in the green pigment dispersion liquid may be C.I. pigment green 58, C.I. pigment green 59, and the like in a color index, which may be used singularly or as a mixture of two or more. In addition, a yellow pigment in the yellow pigment dispersion liquid may be C.I. pigment yellow 139, C.I. pigment yellow 138, C.I. pigment yellow 150, and the like in a color index, which may be used singularly or as a mixture of two or more.

The lower a base line is within the above wavelength range, the higher transmittance (luminance) in a high color region is obtained. As for an absorption peak appearing between 600 nm to 730 nm, a higher peak indicates higher color strength, and herein, a dye of the present invention shows an about 1.5 times as high a peak as and thus has higher color strength than C.I. pigment green 58 and C.I. pigment green 59. Thus, when the dye of the present invention is used along with C.I. pigment green 58, C.I. pigment green 59, C.I. pigment yellow 138, and the like, a higher color coordinate may be realized.

The green pigment and/or the yellow pigment may be used with a dispersing agent in in order to disperse pigments. For example, the pigment may be pretreated with the dispersing agent on the surface or added with the pigment to prepare the composition.

The dispersing agent may be a non-ionic dispersing agent, an anionic dispersing agent, a cationic dispersing agent, and the like. Specific examples of the dispersing agent may be polyalkylene glycol and esters thereof, polyoxyalkylene, polyhydric alcohol ester alkylene oxide addition product, an alcohol alkylene oxide addition product, sulfonate ester, sulfonate salt, a carboxylate ester, a carboxylate salt, an alkylamide alkylene oxide addition product, alkyl amine, and the like, and may be used singularly or as a mixture of two or more.

Commercially available examples of the dispersing agent may include DISPERBYK-101, DISPERBYK-130, DISPERBYK-140, DISPERBYK-160, DISPERBYK-161, DISPERBYK-162, DISPERBYK-163, DISPERBYK-164, DISPERBYK-165, DISPERBYK-166, DISPERBYK-170, DISPERBYK-171, DISPERBYK-182, DISPERBYK-2000, DISPERBYK-2001, and the like made by BYK Co., Ltd.; EFKA-47, EFKA-47EA, EFKA-48, EFKA-49, EFKA-100, EFKA-400, EFKA-450, and the like made by EFKA Chemicals Co.; Solsperse 5000, Solsperse 12000, Solsperse 13240, Solsperse 13940, Solsperse 17000, Solsperse 20000, Solsperse 24000GR, Solsperse 27000, Solsperse 28000, and the like made by Zeneka Co.; or PB711, or PB821 made by Ajinomoto Inc.

The dispersing agent may be included in an amount of, for example, about 0.1 wt % to about 15 wt % based on a total amount of photosensitive resin composition. When the dispersing agent is included within the range, the composition may provide excellent stability, developability, and pattern-forming capability due to improved dispersion properties during manufacture of a black column spacer.

The pigment may be pre-treated using, for example, a water-soluble inorganic salt and a wetting agent. When the pigment is pre-treated, an average particle diameter of the pigment may become finer.

The pre-treatment may be performed by, for example, kneading the pigment with the water-soluble inorganic salt and the wetting agent, and then filtering and washing the kneaded pigment.

The kneading may be performed at a temperature of, for example, about 40° C. to about 100° C., and the filtering and washing may be performed by filtering the pigment after washing away an inorganic salt with water and the like.

Examples of the water-soluble inorganic salt may be sodium chloride, potassium chloride, and the like, but are not limited thereto. The wetting agent may make the pigment to be uniformly mixed with the water-soluble inorganic salt uniformly and be pulverized. Examples of the wetting agent include alkylene glycol monoalkyl ethers such as ethylene glycol monoethylether, propylene glycol monomethylether, diethylene glycol monomethylether, and the like, and alcohols such as ethanol, isopropanol, butanol, hexanol, cyclohexanol, ethylene glycol, diethylene glycol, polyethylene glycol, glycerine polyethylene glycol, and the like. These may be used alone or as a mixture of two or more.

The pigment after the kneading may have an average particle diameter ranging from, for example, about 5 nm to about 200 nm, for example about 5 nm to about 150 nm. When the pigment has an average particle diameter within the range, stability of pigment dispersion liquid may be improved and pixel resolution may not be deteriorated.

A solvent for forming the pigment dispersion liquid may be ethylene glycol acetate, ethylcellosolve, propylene glycol methyletheracetate, ethyl lactate, polyethylene glycol, cyclohexanone, propylene glycol methylether, and the like.

For example, the pigment may be used in a form of pigment dispersion liquid including the dispersing agent and a solvent (described below), and the pigment dispersion liquid may include a solid pigment, a dispersing agent, and a solvent. The solid pigment may be included in an amount of, for example, about 5 wt % to about 20 wt %, for example about 8 wt % to about 15 wt %, based on a total amount of the pigment dispersion liquid.

The pigment dispersion liquid may be included in an amount of, for example, about 10 wt % to about 20 wt %, for example about 12 wt % to about 18 wt %, based on a total amount of the photosensitive resin composition. When the pigment dispersion liquid is included within the ranges, coloring effects, development performance and contrast ratio may be improved.

Binder Resin

The binder resin may include, for example, an acryl-based binder resin.

The acryl-based binder resin may be, for example, a copolymer of a first ethylenic unsaturated monomer and a second ethylenic unsaturated monomer that is copolymerizable therewith, and may be a resin including at least one acryl-based repeating unit.

The first ethylenic unsaturated monomer may be, for example, an ethylenic unsaturated monomer including at least one carboxyl group. Examples of the monomer include (meth)acrylic acid, maleic acid, itaconic acid, fumaric acid, or a combination thereof.

The first ethylenic unsaturated monomer may be included in an amount of, for example, about 5 wt % to about 50 wt %, for example about 10 wt % to about 40 wt %, based on a total amount of the acryl-based binder resin.

The second ethylenic unsaturated monomer may be, for example, an aromatic vinyl compound such as styrene, α-methylstyrene, vinyl toluene, vinylbenzylmethylether and the like; an unsaturated carboxylate ester compound such as methyl(meth)acrylate, ethyl(meth)acrylate, butyl(meth)acrylate, 2-hydroxyethyl(meth)acrylate, 2-hydroxy butyl (meth)acrylate, benzyl(meth)acrylate, cyclohexyl(meth)acrylate, phenyl(meth)acrylate, and the like; an unsaturated amino alkyl carboxylate ester compound such as 2-aminoethyl(meth)acrylate 2-dimethylaminoethyl(meth)acrylate, and the like; a carboxylic acid vinyl ester compound such as vinyl acetate, vinyl benzoate, and the like; an unsaturated glycidyl carboxylate ester compound such as glycidyl(meth)acrylate, and the like; a vinyl cyanide compound such as (meth)acrylonitrile and the like; an unsaturated amide compound such as (meth)acrylamide, and the like; and the like, and may be used singularly or as a mixture of two or more.

Specific examples of the acryl-based binder resin may be a polybenzylmethacrylate copolymer, an acrylic acid/benzylmethacrylate copolymer, a methacrylic acid/benzylmethacrylate copolymer, a methacrylic acid/benzylmethacrylate/styrene copolymer, a methacrylic acid/benzylmethacrylate/2-hydroxyethylmethacrylate copolymer, a methacrylic acid/benzylmethacrylate/styrene/2-hydroxyethylmethacrylate copolymer, and the like, but are not limited thereto. These may be used singularly or as a mixture of two or more.

A weight average molecular weight of the binder resin may be, for example, about 3,000 g/mol to about 150,000 g/mol, for example about 5,000 g/mol to about 50,000 g/mol, for example about 20,000 g/mol to about 30,000 g/mol. When the binder resin has a weight average molecular weight within the range, the photosensitive resin composition may exhibit good physical and chemical properties, appropriate viscosity, and close contacting properties with a substrate during manufacture of a color filter.

The binder resin may be included in an amount of, for example, about 1 wt % to about 30 wt %, for example about 1 wt % to about 20 wt %, based on a total amount of the photosensitive resin composition. When the binder resin is included within the above range, developability may be improved and excellent surface smoothness may be improved due to improved cross-linking during the manufacture of a color filter.

Photopolymerizable Compound

The photopolymerizable compound may be, for example, a mono-functional or multi-functional ester of (meth)acrylic acid including at least one ethylenic unsaturated double bond.

The photopolymerizable compound having the ethylenic unsaturated double bond may produce a desirable level of polymerization during exposure in a pattern-forming process, and may help form a pattern having excellent heat resistance, light resistance, and chemical resistance.

Specific examples of the photopolymerizable compound may be ethylene glycol di(meth)acrylate, diethylene glycol di(meth)acrylate, triethylene glycol di(meth)acrylate, propylene glycol di(meth)acrylate, neopentyl glycol di(meth)acrylate, 1,4-butanediol di(meth)acrylate, 1,6-hexanediol di(meth)acrylate, bisphenol A di(meth)acrylate, pentaerythritol di(meth)acrylate, pentaerythritol tri(meth)acrylate, pentaerythritol tetra(meth)acrylate, pentaerythritol hexa(meth)acrylate, dipentaerythritol di(meth)acrylate, dipentaerythritol tri(meth)acrylate, dipentaerythritol penta(meth)acrylate, dipentaerythritol hexa(meth)acrylate, bisphenol A epoxy(meth)acrylate, ethylene glycol monomethylether (meth)acrylate, trimethylol propane tri(meth)acrylate, tris (meth)acryloyloxyethyl phosphate, novolac epoxy (meth)acrylate, and the like.

Commercially available examples of the photopolymerizable compound may be as follows. The mono-functional (meth)acrylic acid ester may include Aronix M-101®, M-111®, M-114® (Toagosei Chemistry Industry Co., Ltd.); KAYARAD TC-110S®, TC-120S® (Nippon Kayaku Co., Ltd.); V-158®, V-2311® (Osaka Organic Chemical Ind., Ltd.), and the like. Examples of a difunctional (meth)acrylic acid ester may include Aronix M-210®, M-240®, M-6200® (Toagosei Chemistry Industry Co., Ltd.), KAYARAD HDDA®, HX-220®, R-604® (Nippon Kayaku Co., Ltd.), V-260®, V-312®, V-335 HP® (Osaka Organic Chemical Ind., Ltd.), and the like. Examples of a tri-functional (meth) acrylic acid ester may include Aronix M-309®, M-400®, M-405®, M-450®, M-7100®, M-8030®, M-8060® (Toagosei Chemistry Industry Co., Ltd.), KAYARAD TMPTA®, DPCA-20®, DPCA-30®, DPCA-60®, DPCA-120® (Nippon Kayaku Co., Ltd.), V-295®, V-300®, V-360®, V-GPT®, V-3PA®, V-400® (Osaka Yuki Kayaku Kogyo Co. Ltd.), and the like. These may be used singularly or as a mixture of two or more.

The photopolymerizable compound may be treated with an acid anhydride to improve developability.

The photopolymerizable compound may be included in an amount of, for example, about 1 wt % to about 15 wt %, for example about 5 wt % to about 10 wt % based on a total amount of the photosensitive resin composition. When the photopolymerizable compound is included within the range, the photopolymerizable compound may be cured to a desirable level during exposure in a pattern-forming process, may help provide excellent reliability, and developability for alkali developing solution may be improved.

Photopolymerization Initiator

The photopolymerization initiator may be a suitable photopolymerization initiator generally used in a photosensitive resin composition, for example an acetophenone-based compound, a benzophenone-based compound, a thioxanthone-based compound, a benzoin-based compound, an oxime-based compound, and the like.

Examples of the acetophenone-based compound may be 2,2'-diethoxy acetophenone, 2,2'-dibutoxy acetophenone, 2-hydroxy-2-methylpropinophenone, p-t-butyltrichloro acetophenone, p-t-butyldichloro acetophenone, 4-chloro acetophenone, 2,2'-dichloro-4-phenoxy acetophenone, 2-methyl-1-(4-(methylthio)phenyl)-2-morpholinopropan-1-one, 2-benzyl-2-dimethylamino-1-(4-morpholinophenyl)-butan-1-one, and the like.

Examples of the benzophenone-based compound may be benzophenone, benzoyl benzoate, methyl benzoyl benzoate, 4-phenyl benzophenone, hydroxy benzophenone, acrylated benzophenone, 4,4'-bis(dimethyl amino)benzophenone, 4,4'-bis(diethylamino)benzophenone, 4,4'-dimethylaminobenzophenone, 4,4'-dichlorobenzophenone, 3,3'-dimethyl-2-methoxybenzophenone, and the like.

Examples of the thioxanthone-based compound may be thioxanthone, 2-methylthioxanthone, isopropyl thioxanthone, 2,4-diethyl thioxanthone, 2,4-diisopropyl thioxanthone, 2-chlorothioxanthone, and the like.

Examples of the benzoin-based compound may be benzoin, benzoin methyl ether, benzoin ethyl ether, benzoin isopropyl ether, benzoin isobutyl ether, benzyldimethylketal, and the like.

Examples of the triazine-based compound may be 2,4,6-trichloro-s-triazine, 2-phenyl 4,6-bis(trichloromethyl)-s-triazine, 2-(3', 4'-dimethoxystyryl)-4,6-bis(trichloromethyl)-s-triazine, 2-(4'-methoxynaphthyl)-4,6-bis(trichloromethyl)-s-triazine, 2-(p-methoxyphenyl)-4,6-bis(trichloromethyl)-s-triazine, 2-(p-tolyl)-4,6-bis(trichloro methyl)-s-triazine, 2-biphenyl 4,6-bis(trichloro methyl)-s-triazine, bis(trichloromethyl)-6-styryl-s-triazine, 2-(naphthol-yl)-4,6-bis(trichloromethyl)-s-triazine, 2-(4-methoxynaphthol-yl)-4,6-bis(trichloromethyl)-s-triazine, 2-4-bis(trichloromethyl)-6-piperonyl-s-triazine, 2-4-bis(trichloromethyl)-6-(4-methoxystyryl)-s-triazine, and the like.

Examples of the oxime-based compound may be O-acyloxime-based compound, 2-(O-benzoyloxime)-1-[4-(phenylthio)phenyl]-1,2-octandione, 1-(O-acetyloxime)-1-[9-ethyl-6-(2-methylbenzoyl)-9H-carbazol-3-yl]ethanone, O-ethoxycarbonyl-a-oxyamino-1-phenylpropan-1-one, and the like. Specific examples of the O-acyloxime-based compound may be 1,2-octandione, 2-dimethylamino-2-(4-methylbenzyl)-1-(4-morpholin-4-yl-phenyl)-butan-1-one, 1-(4-phenylsulfanyl phenyl)-butane-1,2-dione 2-oxime-O-benzoate, 1-(4-phenylsulfanyl phenyl)-octane-1,2-dione 2-oxime-O-benzoate, 1-(4-phenylsulfanyl phenyl)-octan-1-one oxime-O-acetate, 1-(4-phenylsulfanyl phenyl)-butan-1-one oxime-O-acetate, and the like.

The photopolymerization initiator may further include, for example, a carbazole-based compound, a diketone-based compound, a sulfonium borate-based compound, a diazo-based compound, an imidazole-based compound, a biimidazole-based compound, a fluorene-based compound, and the like in addition to the compound.

The photopolymerization initiator may be used with a photosensitizer capable of causing a chemical reaction by absorbing light and becoming excited, and then transferring its energy.

Examples of the photosensitizer may be tetraethylene glycol bis-3-mercapto propionate, pentaerythritol tetrakis-3-mercapto propionate, dipentaerythritol tetrakis-3-mercapto propionate, and the like.

The photopolymerization initiator be included in an amount of, for example, about 0.01 wt % to about 10 wt %, for example about 0.1 wt % to about 5 wt % based on a total amount of the photosensitive resin composition. When the photopolymerization initiator is included within the range, excellent reliability may be secured due to sufficiently curing during exposure in a pattern-forming process, a pattern may have excellent resolution and close-contacting properties as well as excellent heat resistance, light resistance, and chemical resistance, and transmittance may be prevented from deterioration due to a non-reaction initiator.

Solvent

The solvent is a material having compatibility with the compound according to an embodiment, the pigment, the binder resin, the photopolymerizable compound, and the photopolymerization initiator but not reacting therewith.

Examples of the solvent may include alcohols such as methanol, ethanol, and the like; ethers such as dichloroethyl ether, n-butyl ether, diisoamyl ether, methylphenyl ether, tetrahydrofuran, and the like; glycol ethers such as ethylene glycol monomethylether, ethylene glycol monoethylether, and the like; cellosolve acetates such as methyl cellosolve acetate, ethyl cellosolve acetate, diethyl cellosolve acetate, and the like; carbitols such as methylethyl carbitol, diethyl carbitol, diethylene glycol monomethylether, diethylene glycol monoethylether, diethylene glycol dimethylether, diethylene glycol methylethylether, diethylene glycol diethylether, and the like; propylene glycol alkylether acetates such as propylene glycol methylether acetate, propylene glycol propylether acetate, and the like; aromatic hydrocarbons such as toluene, xylene and the like; ketones such as methylethylketone, cyclohexanone, 4-hydroxy-4-methyl-2-pentanone, methyl-n-propylketone, methyl-n-butylketone, methyl-n-amylketone, 2-heptanone, and the like; saturated aliphatic monocarboxylic acid alkyl esters such as ethyl acetate, n-butyl acetate, isobutyl acetate, and the like; lactate esters such as methyl lactate, ethyl lactate, and the like; oxy acetic acid alkyl esters such as oxy methyl acetate, oxy ethyl acetate, butyl oxyacetate, and the like; alkoxy acetic acid alkyl esters such as methoxy methyl acetate, methoxy ethyl acetate, methoxy butyl acetate, ethoxy methyl acetate, ethoxy ethyl acetate, and the like; 3-oxy propionic acid alkyl esters such as 3-oxy methyl propionate, 3-oxy ethyl propionate, and the like; 3-alkoxy propionic acid alkyl esters such as 3-methoxy methyl propionate, 3-methoxy ethyl propionate, 3-ethoxy ethyl propionate, 3-ethoxy methyl propionate, and the like; 2-oxy propionic acid alkyl esters such as 2-oxy methyl propionate, 2-oxy ethyl propionate, 2-oxy propyl propionate, and the like; 2-alkoxy propionic acid alkyl esters such as 2-methoxy methyl propionate, 2-methoxy ethyl propionate, 2-ethoxy ethyl propionate, 2-ethoxy methyl propionate, and the like; 2-oxy-2-methyl propionic acid esters such 2-oxy-2-methyl methyl propionate, 2-oxy-2-methyl ethyl propionate, and the like, monooxy monocarboxylic acid alkyl esters of 2-alkoxy-2-methyl alkyl propionates such as 2-methoxy-2-methyl methyl propionate, 2-ethoxy-2-methyl ethyl propionate, and the like; esters such as 2-hydroxy ethyl propionate, 2-hydroxy-2-methyl ethyl propionate, hydroxy ethyl acetate, 2-hydroxy-3-methyl methyl butanoate, and the like; ketonate esters such as ethyl pyruvate, and the like. Additionally, high boiling point solvent such as N-methylformamide, N,N-dimethylformamide, N-methylformanilide, N-methylacetamide, N,N-dimethylacetamide, N-methylpyrrolidone, dimethylsulfoxide, benzylethylether, dihexylether, acetylacetone, isophorone, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate, phenyl cellosolve acetate, and the like may be also used.

Considering miscibility and reactivity, glycol ethers such as ethylene glycol monoethylether, and the like; ethylene glycol alkylether acetates such as ethyl cellosolve acetate, and the like; esters such as 2-hydroxy ethyl propionate, and the like; carbitols such as diethylene glycol monomethylether, and the like; propylene glycol alkylether acetates such as propylene glycol methylether acetate, propylene glycol propylether acetate, and the like and ketones such as cyclohexanone, and the like may be used.

The solvent may be used in, for example, a balance amount or about 30 wt % to about 80 wt %, based on a total amount of the photosensitive resin composition. When the solvent is included within the range, the photosensitive resin composition may have an appropriate viscosity resulting in improvement of coating characteristics of a color filter.

Other Additives

The photosensitive resin composition according to an embodiment may include additives such as malonic acid; 3-amino-1,2-propanediol; a silane-based coupling agent including a vinyl group or a (meth)acryloxy group; a leveling agent; a surfactant; and a radical polymerization initiator in order to prevent stains or spots during the coating, to adjust leveling, or to prevent pattern residue due to non-development.

The additives may be controlled depending on desired properties.

The coupling agent may be, for example, a silane-based coupling agent, and examples of the silane-based coupling agent may be trimethoxysilyl benzoic acid, γ-methacryl oxypropyl trimethoxysilane, vinyl triacetoxysilane, vinyl trimethoxysilane, γ-isocyanate propyl triethoxysilane, γ-glycidoxy propyl trimethoxysilane, β-(3,4-epoxycyclohexyl) ethyltrimethoxysilane, and the like. These may be used singularly or in a mixture of two or more.

The silane-based coupling agent may be included in an amount of, for example, about 0.01 parts by weight to about 10 parts by weight, based on a total amount of the photosensitive resin composition.

The photosensitive resin composition according to an example embodiment may include, for example, a surfactant, for example a fluorine-based surfactant.

Examples of the fluorine-based surfactant may include F-482, F-484, F-478, and the like made by DIC Co., Ltd., but are not limited thereto.

The surfactant may be included in an amount of, for example, about 0.001 wt % to about 5 wt %, for example about 0.01 wt % to about 2 wt %, based on a total amount of photosensitive resin composition. Providing the surfactant in an amount that is in the ranges may help prevent generation of foreign particles after development.

The photosensitive resin composition according to an example embodiment may include, for example, an epoxy compound, which may improve adhesion to substrate.

Examples of the epoxy compound may include phenol novolac epoxy compound, tetramethyl biphenyl epoxy compound, bisphenol A epoxy compound, cycloaliphatic epoxy compound or a combination thereof.

The epoxy compound may be included in an amount of, for example, about 0.01 parts by weight to about 20 parts by weight, for example about 0.1 parts by weight to about 10 parts by weight, based on 100 parts by weight of the photosensitive resin composition. When the amount is in the ranges, adhesion and storage may be enhanced.

In example embodiments, the photosensitive resin composition may additives such as an antioxidant, a stabilizer, and the like in a predetermined amount that does not deteriorate properties of the photosensitive resin composition.

According to another example embodiment, a color filter manufactured using the photosensitive resin composition according to the embodiment is provided.

An example method of manufacturing the color filter is as follows.

The photosensitive resin composition may be coated to form a 0.5 μm to 10 μm-thick photosensitive resin composition layer on a glass substrate in an appropriate method such as spin coating, roller coating, spray coating, and the like.

Subsequently, the substrate having the photosensitive resin composition layer may be irradiated with light to form a pattern required for a color filter. The irradiation may be performed by using, for example, UV, an electron beam, or an X-ray as a light source. The UV may be radiated, for example, in a region of 190 nm to 450 nm, for example, 200 nm to 400 nm. The radiation may be performed by further using a photoresist mask. After performing the radiation process in this way, the photosensitive resin composition layer exposed to the light source may be treated with a developing solution. For example, a non-exposed region in the photosensitive resin composition layer may be dissolved to leave the pattern for a color filter. This process may be repeated, for example, as many times as the number of colors, to obtain a color filter having a desired pattern. In addition, when the image pattern obtained through development in the above process is cured by reheating or radiating an actinic ray thereinto, crack resistance, solvent resistance, and the like may be improved.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS OF COMPOUNDS

Synthesis Example 1: Synthesis of 4-(biphenyl-2-yloxy)-3,5,6-trichloro-phthalonitrile 5 g of 3,4,5,6-tetrachlorophthalonitrile, 3.21 g of 2-phenylphenol, 3.9 g of $K_2CO_3$, and 25 ml of acetone were put in a 100 ml flask, and then stirred while heated at 70° C. When the reaction was complete, the resultant was filtered and washed with acetone, and a liquid therefrom was distilled to obtain a solid. Herein, the obtained solid was dissolved in a small amount of dichloromethane, and then several times washed with hexane, filtered, and vacuum-dried to obtain 4-(biphenyl-2-yloxy)-3,5,6-trichloro-phthalonitrile.

Synthesis Example 2: Synthesis of 3,4,6-trichloro-5-(2,6-dichloro-phenoxy)-phthalonitrile 5 g of 3,4,5,6-tetrachlorophthalonitrile, 3.06 g of 2,6-dichlorophenol, 3.9 g of $K_2CO_3$, and 25 ml of acetone were put in a 100 ml flask, and then stirred while heated at 70° C. When the reaction was complete, the resultant was filtered and washed with acetone, and a liquid therefrom was distilled to obtain a solid. Herein, the obtained solid was dissolved in a small amount of dichloromethane, and then several times washed with hexane, filtered, and vacuum-dried to obtain 3,4,6-trichloro-5-(2,6-dichloro-phenoxy)-phthalonitrile.

Synthesis Example 3: Synthesis of 3,4,6-trichloro-5-(2,6-dibromo-phenoxy)-phthalonitrile 5 g of 3,4,5,6-tetrachlorophthalonitrile, 4.75 g of 2,6-dibromophenol, 3.9 g of $K_2CO_3$, and 25 ml of N,N-dimethyl formamide were put in a 100 ml flask and stirred while heated at 70° C. When the reaction was complete, EA (ethyl acetate) was used for an extraction. After the extraction, the resultant was concentrated to obtain a solid. The obtained solid was dissolved in a small amount of dichloromethane, several times washed with hexane, filtered, and vacuum-dried to obtain 3,4,6-trichloro-5-(2,6-dibromo-phenoxy)-phthalonitrile.

Synthesis Example 4: Synthesis of 3,4,6-trichloro-5-(2,6-difluoro-phenoxy)-phthalonitrile 5 g of 3,4,5,6-tetrachlorophthalonitrile, 2.45 g of 2,6-difluorophenol, 3.9 g of $K_2CO_3$, and 25 ml of N,N-dimethyl formamide were put in s 100 ml flask, and then stirred while heated at 70° C. When the reaction was complete, EA (ethyl acetate) was used for an extraction. After the extraction, the resultant was concentrated to obtain a solid. Herein, the obtained solid was dissolved in a small amount of dichloromethane, and then several times washed with hexane, filtered, and vacuum-dried to obtain 3,4,6-trichloro-5-(2,6-difluoro-phenoxy)-phthalonitrile.

Synthesis Example 5: Synthesis of 3,4,6-trichloro-5-(2-chloro-phenoxy)-phthalonitrile 5 g of 3,4,5,6-tetrachlorophthalonitrile, 2.41 g of 2-chlorophenol, 3.9 g of $K_2CO_3$, and 25 ml of acetone were put in a 100 ml flask, and then stirred while heated at 70° C. When the reaction was complete, the resultant was filtered and washed with acetone, and a liquid therefrom was distillated to obtain a solid. Herein, the obtained solid was dissolved in a small amount of dichloromethane, several times washed with hexane, filtered, and then vacuum-dried to obtain 3,4,6-trichloro-5-(2-chloro-phenoxy)-phthalonitrile.

Synthesis Example 6: Synthesis of 3,4,6-trichloro-5-(2-bromo-phenoxy)-phthalonitrile 5 g of 3,4,5,6-tetrachlorophthalonitrile, 3.25 g of 2-bromophenol, 3.9 g of $K_2CO_3$, and 25 ml of N,N-dimethyl formamide were put in a 100 ml flask, and then stirred while heated at 70° C. When the reaction was complete, EA (ethyl acetate) was used for an extraction. After the extraction, the resultant was concentrated to obtain a solid. Herein, the obtained solid was dissolved in an small amount of dichloromethane, several times washed with hexane, filtered, and vacuum-dried to obtain 3,4,6-trichloro-5-(2-bromo-phenoxy)-phthalonitrile.

Synthesis Example 7: Synthesis of 3,4,6-trichloro-5-(2-fluoro-phenoxy)-phthalonitrile 5 g of 3,4,5,6-tetrachlorophthalonitrile, 2.10 g of 2-fluorophenol, 3.9 g of $K_2CO_3$, and 25 ml of N,N-dimethyl formamide were put in a 100 ml flask, and then stirred while heated at 70° C. When the reaction was complete, EA (ethyl acetate) was used for an extraction. After the extraction, the resultant was concentrated to obtain a solid. The obtained solid was dissolved in a small amount of dichloromethane, several times washed with hexane, filtered, and vacuum-dried to obtain 3,4,6-trichloro-5-(2-fluoro-phenoxy)-phthalonitrile.

Synthesis Example 8: Synthesis of 3,4,6-trichloro-5-(2,5-dichloro-phenoxy)-phthalonitrile 5 g of 3,4,5,6-tetrachlorophthalonitrile, 3.06 g of 2,5-dichlorophenol, 3.9 g of $K_2CO_3$, and 25 ml of acetone were put in a 100 ml flask, and then stirred while heated at 70° C. When the reaction was complete, the resultant was filtered and washed with acetone, and a liquid therefrom was distillated to obtain a solid. Herein, the obtained solid was dissolved in a small amount of dichloromethane, several times washed with hexane, filtered, and vacuum-dried to obtain 3,4,6-trichloro-5-(2,5-dichloro-phenoxy)-phthalonitrile.

Synthesis Example 9: Synthesis of Compound Represented by Chemical Formula 5

1.5 g of the 4-(biphenyl-2-yloxy)-3,5,6-trichloro-phthalonitrile of Synthesis Example 1, 0.49 g of the 3,4,6-trichloro-5-(2,6-dichloro-phenoxy)-phthalonitrile of Synthesis Example 2, 1.52 g of 1,8-diazabicycloundec-7-ene, and 14 g of 1-pentenol were put in a 100 mL flask, and then heated at 90° C., after the solid was dissolved, 0.23 g of zinc acetate was added thereto, and the mixture was stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid to dissolve it, and methanol was added thereto for crystallization. The crystallized solid was filtered and vacuum-dried to obtain a compound represented by Chemical Formula 5.

[Chemical Formula 5]

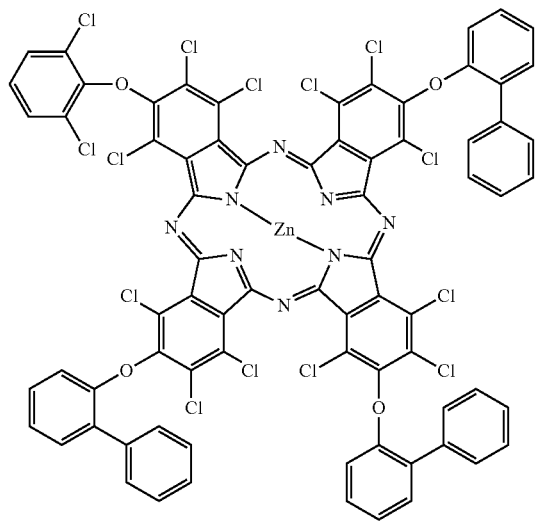

Maldi-TOF MS: 1656.79 m/z

Synthesis Example 10: Synthesis of Compound Represented by Chemical Formula 6

1.6 g of the 4-(biphenyl-2-yloxy)-3,5,6-trichloro-phthalonitrile according to Synthesis Example 1, 1.5 g of the 3,4,6-trichloro-5-(2,6-dichloro-phenoxy)-phthalonitrile according to Synthesis Example 2, 1.74 g of 1,8-diazabicycloundec-7-ene, and 14 g of 1-pentenol were put in a 100 mL flask and heated at 90° C., after the solids were dissolved, 0.34 g of zinc acetate was added thereto, and the mixture stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid and dissolve it, and methanol was added thereto for crystallization. The crystallized solid was filtered and vacuum-dried to obtain a compound represented by Chemical Formula 6.

[Chemical Formula 6]

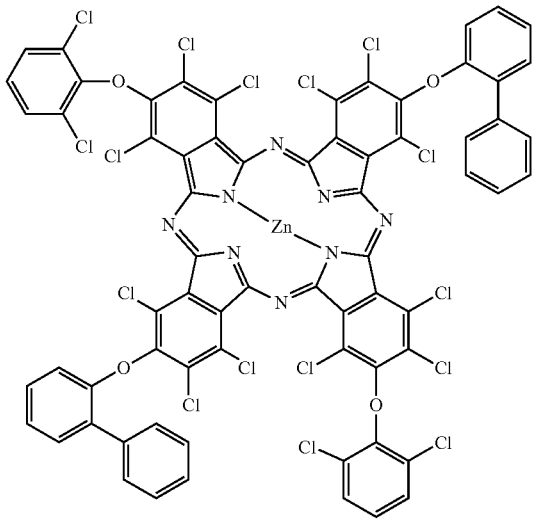

Maldi-TOF MS: 1649.57 m/z

Synthesis Example 11: Synthesis of Compound Represented by Chemical Formula 7

1 g of the 4-(biphenyl-2-yloxy)-3,5,6-trichloro-phthalonitrile of Synthesis Example 1, 2.9 g of the 3,4,6-trichloro-5-(2,6-dichloro-phenoxy)-phthalonitrile Synthesis Example 2, 3 g of 1,8-diazabicycloundec-7-ene, and 27 g of 1-pentenol were put in a 100 mL flask and heated at 90° C., after dissolving the solid, 0.45 g of zinc acetate was added thereto, and the mixture was stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid to dissolve it, and methanol was added thereto for crystallization. The crystallized solid was filtered and vacuum-dried to obtain a compound represented by Chemical Formula 7.

[Chemical Formula 7]

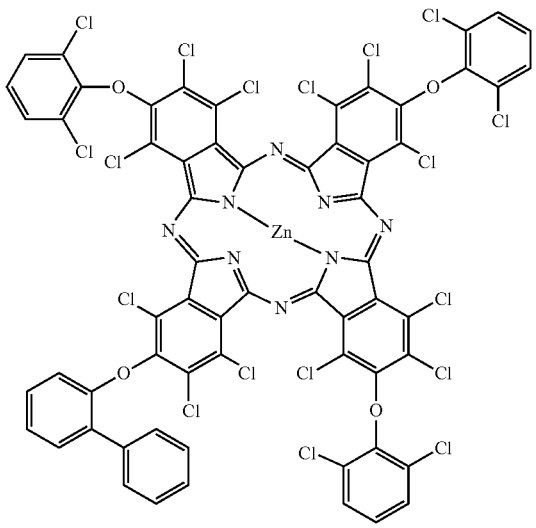

Maldi-TOF MS: 1642.36 m/z

Synthesis Example 12: Synthesis of Compound Represented by Chemical Formula 8

1.5 g of the 3,4,6-trichloro-5-(2,6-dichloro-phenoxy)-phthalonitrile of Synthesis Example 2, 0.87 g of 1,8-diazabicycloundec-7-ene, and 7 g of 1-pentenol were put in a 100 mL flask, and then heated at 90° C., after the solid was dissolved, 0.17 g of zinc acetate was added thereto, and the mixture was stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid to dissolve it, and methanol was added thereto for crystallization. The crystallized solid was filtered and vacuum-dried to obtain a compound represented by Chemical Formula 8.

[Chemical Formula 8]

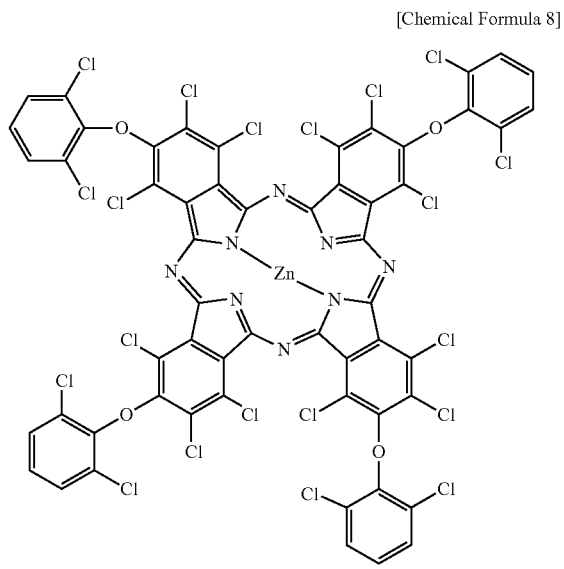

Maldi-TOF MS: 1635.14 m/z

Synthesis Example 13: Synthesis of Compound Represented by Chemical Formula 9

1.5 g of the 3,4,6-trichloro-5-(2,6-dibromo-phenoxy)-phthalonitrile of Synthesis Example 3, 0.87 g of 1,8-diazabicycloundec-7-ene, and 7 g of 1-pentenol were put in a 100 mL flask, and then heated at 90° C., after the solid was dissolved, 0.17 g of zinc acetate was added thereto, and the mixture was stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid, and methanol was used for crystallization. The crystallized solid was filtered and vacuum-dried to obtain a compound represented by Chemical Formula 9.

[Chemical Formula 9]

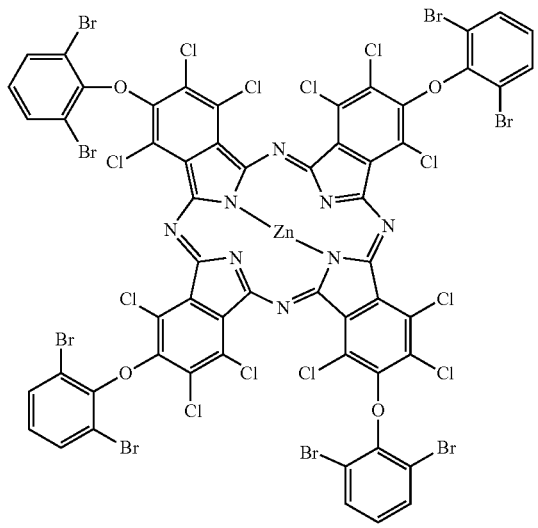

Maldi-TOF MS: 1990.78 m/z

Synthesis Example 14: Synthesis of Compound Represented by Chemical Formula 10

1.5 g of the 3,4,6-trichloro-5-(2,6-difluoro-phenoxy)-phthalonitrile of Synthesis Example 4, 0.87 g of 1,8-diazabicycloundec-7-ene, and 7 g of 1-pentenol were put in a 100 mL flask and heated at 90° C., after the solid was dissolved, 0.17 g of zinc acetate was added thereto, and the mixture was stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid, and methanol was added thereto for crystallization. The crystallized solid was filtered and vacuum-dried to obtain a compound represented by Chemical Formula 10.

[Chemical Formula 10]

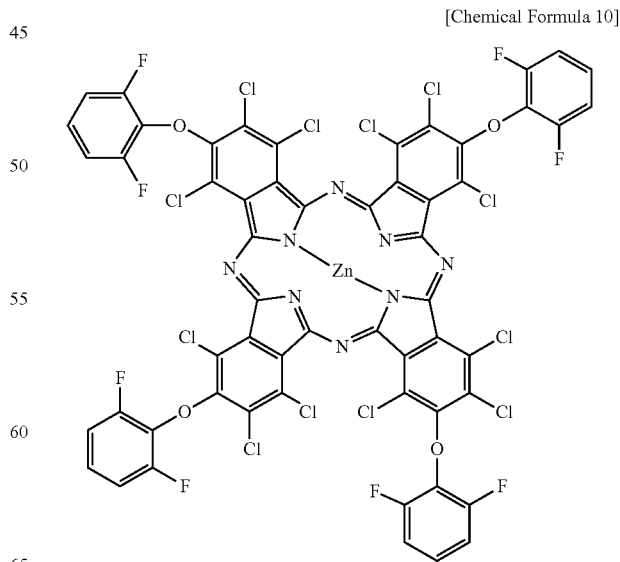

Maldi-TOF MS: 1503.53 m/z

Synthesis Example 15: Synthesis of Compound Represented by Chemical Formula 11

1.5 g of the 3,4,6-trichloro-5-(2-chloro-phenoxy)-phthalonitrile of Synthesis Example 5, 0.87 g of 1,8-diazabicycloundec-7-ene, and 7 g of 1-pentenol were put in a 100 mL flask and heated at 90° C., after the solid was dissolved, 0.17 g of zinc acetate was added thereto, and the mixture was stirred while heated at 140° C. When the reaction was complete, methanol was used for a precipitation, and a precipitate was filtered and vacuum-dried. The dried solid was purified through column chromatography. Then, dichloromethane was appropriately added to the purified solid to dissolve it, and methanol was added thereto for crystallization. The crystallized solid was filtered and vacuum-dried to obtain a compound represented by Chemical Formula 11.

[Chemical Formula 11]

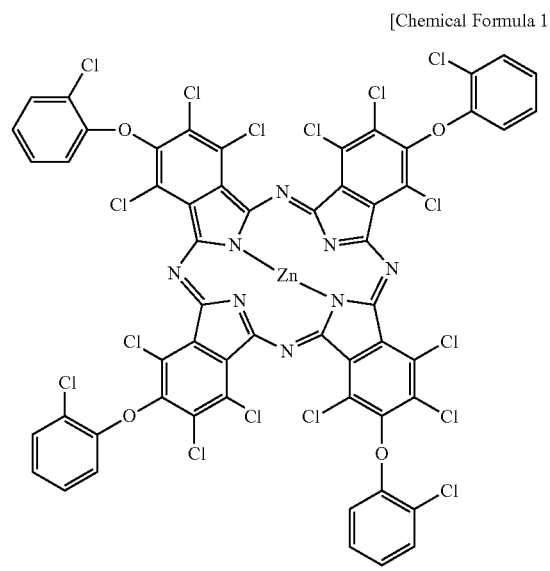

Maldi-TOF MS: 1497.38 m/z

Synthesis Example 16: Synthesis of Compound Represented by Chemical Formula 12

1.5 g of the 3,4,6-trichloro-5-(2-bromo-phenoxy)-phthalonitrile of Synthesis Example 6, 0.87 g of 1,8-diazabicycloundec-7-ene, and 7 g of 1-pentenol were put in a 100 mL flask and heated at 90° C., after the solid was dissolved, 0.17 g of zinc acetate was added thereto, and the mixture was stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid to dissolve it, and methanol was added thereto for crystallization. The crystallized solid was filtered and vacuum-dried to obtain a compound represented by Chemical Formula 12.

[Chemical Formula 12]

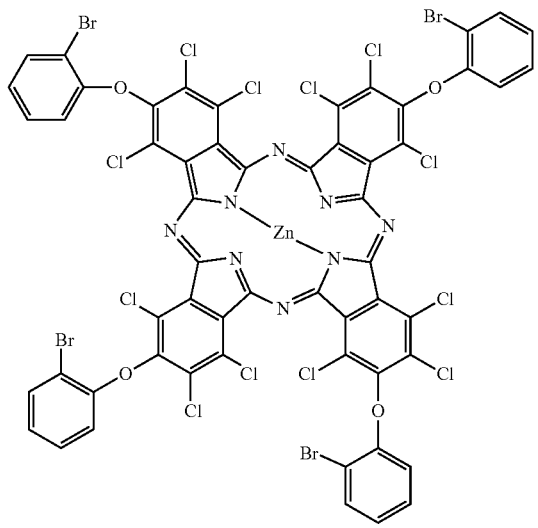

Maldi-TOF MS: 1675.19 m/z

Synthesis Example 17: Synthesis of Compound Represented by Chemical Formula 13

1.5 g of the 3,4,6-trichloro-5-(2-fluoro-phenoxy)-phthalonitrile of Synthesis Example 7, 0.87 g of 1,8-diazabicycloundec-7-ene, and 7 g of 1-pentenol were put in a 100 mL flask and heated at 90° C., after dissolving the solid, 0.17 g of zinc acetate was added thereto, and the mixture was stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid to dissolve it, and methanol was added thereto for crystallization. The crystallized solid was filtered and vacuum-dried to obtain a compound represented by Chemical Formula 13.

[Chemical Formula 13]

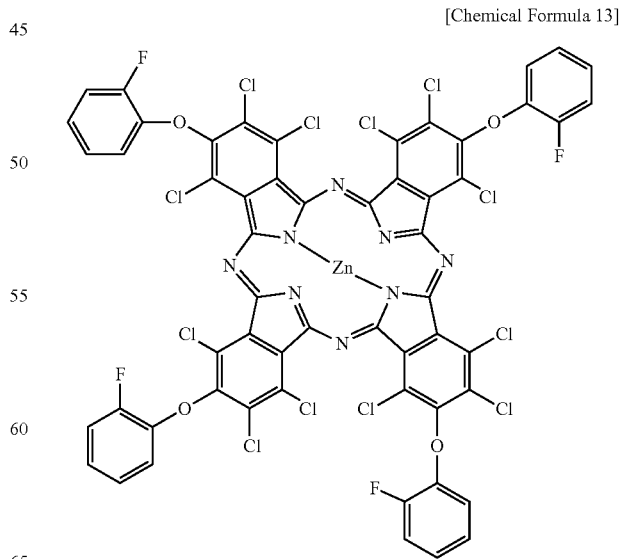

Maldi-TOF MS: 1431.57 m/z

Synthesis Example 18: Synthesis of Compound Represented by Chemical Formula 14

1.6 g of the 4-(biphenyl-2-yloxy)-3,5,6-trichloro-phthalonitrile of Synthesis Example 1, 1.5 g of the 3,4,6-trichloro-5-(2,5-dichloro-phenoxy)-phthalonitrile of Synthesis Example 8, 1.74 g of 1,8-diazabicycloundec-7-ene, and 14 g of 1-pentenol were put in a 100 mL flask and heated at 90° C., after dissolving the solid, 0.34 g of zinc acetate was added thereto, and the mixture was stirred while heated at 140° C. When the reaction was complete, methanol was used for a precipitation, and a precipitate therefrom was filtered and vacuum-dried. The dried solid was purified through column chromatography. Then, dichloromethane was appropriately added to the purified solid to dissolve it, and methanol was added thereto for crystallization. The crystallized solid was filtered and vacuum-dried to obtain a compound represented by Chemical Formula 14.

[Chemical Formula 14]

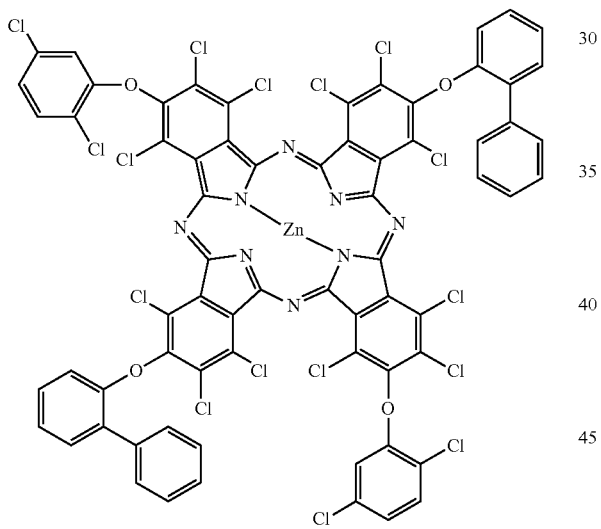

Maldi-TOF MS: 1649.57 m/z

Comparative Synthesis Example 1: Synthesis of Compound Represented by Chemical Formula X 1 g of 4-(2-sec-Butyl-phenoxy)-3,5,6-trichloro-phthalonitrile, 0.30 g of 1,8-diazabicycloundec-7-ene, 7 g of 1-pentenol, and 0.12 g of zinc acetate were put in a 100 mL flask and stirred while heated at 140° C. When the reaction was complete, the resultant was concentrated and purified through column chromatography. The purified liquid was concentrated to obtain a solid. The crystallized solid was vacuum-dried to obtain a compound represented by Chemical Formula X.

[Chemical Formula X]

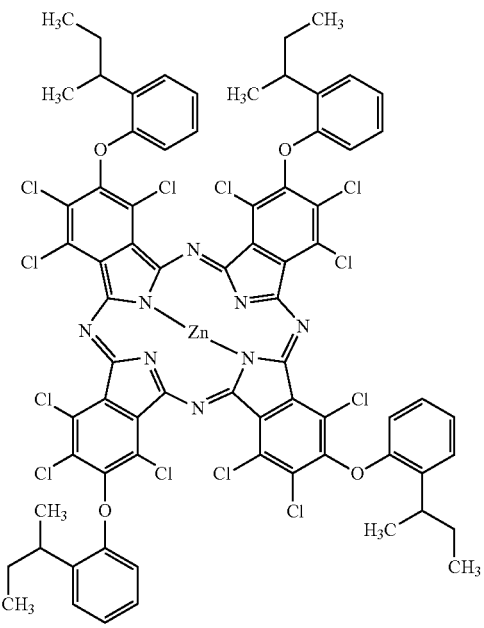

Maldi-TOF MS: 1584.04 m/z

Synthesis of Photosensitive Resin Composition

Example 1

A photosensitive resin composition according to Example 1 was prepared by mixing the following components with the compositions shown in Table 1.

Specifically, a photopolymerization initiator was dissolved in a solvent, the solution was stirred at room temperature for 2 hours, a binder resin and a photopolymerizable compound was added thereto, and the mixture was stirred at room temperature for 2 hours. Subsequently, the compound (represented by Chemical Formula 5) of Synthesis Example 9 and a pigment (in a pigment dispersion liquid state) as a colorant were added to the reactant, and the mixture was stirred at room temperature for 1 hour. Then, a product therefrom was three times filtered to remove impurities to prepare a photosensitive resin composition.

TABLE 1

| Formulation materials | | | Amount |
|---|---|---|---|
| Colorant | Dye | Compound of Synthesis Example 9 | 5.0 |
| | Pigment dispersion liquid | Pigment Y138 pigment dispersion liquid | 15.0 |
| Binder resin | | (A)/(B) = 15/85 (w/w), molecular weight (Mw) = 22,000 g/mol (A): methacrylic acid (B): benzylmethacrylate | 3.5 |
| Photopolymerizable compound | | Dipentaerythritolhexaacrylate (DPHA) | 8.0 |
| Photopolymerization initiator | | 1,2-octandione | 1.0 |
| | | 2-dimethylamino-2-(4-methylbenzyl)-1-(4-morpholin-4-yl-phenyl)-butan-1-one | 0.5 |

TABLE 1-continued

| Formulation materials | | Amount |
|---|---|---|
| Solvent | Cyclohexanone | 37.0 |
| | PGMEA (Propylene Glycol Monomethyl Ether Acetate) | 30.0 |
| | Total | 100.00 |

(unit: wt %)

Example 2

A photosensitive resin composition was prepared according to the same method as Example 1 except for using the compound of Synthesis Example 10 (represented by Chemical Formula 6) instead of the compound of Synthesis Example 9 (represented by Chemical Formula 5).

Example 3

A photosensitive resin composition was prepared according to the same method as Example 1 except for using the compound of Synthesis Example 11 (represented by Chemical Formula 7) instead of the compound of Synthesis Example 9 (represented by Chemical Formula 5).

Example 4

A photosensitive resin composition was prepared according to the same method as Example 1 except for using the compound of Synthesis Example 12 (represented by Chemical Formula 8) instead of the compound of Synthesis Example 9 (represented by Chemical Formula 5).

Example 5

A photosensitive resin composition was prepared according to the same method as Example 1 except for using the compound of Synthesis Example 13 (represented by Chemical Formula 9) instead of the compound of Synthesis Example 9 (represented by Chemical Formula 5).

Example 6

A photosensitive resin composition was prepared according to the same method as Example 1 except for using the compound of Synthesis Example 14 (represented by Chemical Formula 10) instead of the compound of Synthesis Example 9 (represented by Chemical Formula 5).

Example 7

A photosensitive resin composition was prepared according to the same method as Example 1 except for using the compound of Synthesis Example 15 (represented by Chemical Formula 11) instead of the compound of Synthesis Example 9 (represented by Chemical Formula 5).

Example 8

A photosensitive resin composition was prepared according to the same method as Example 1 except for using the compound of Synthesis Example 16 (represented by Chemical Formula 12) instead of the compound of Synthesis Example 9 (represented by Chemical Formula 5).

Example 9

A photosensitive resin composition was prepared according to the same method as Example 1 except for using the compound of Synthesis Example 17 (represented by Chemical Formula 13) instead of the compound of Synthesis Example 9 (represented by Chemical Formula 5).

Example 10

A photosensitive resin composition was prepared according to the same method as Example 1 except for using the compound of Synthesis Example 18 (represented by Chemical Formula 14) instead of the compound of Synthesis Example 9 (represented by Chemical Formula 5).

Example 11

A photosensitive resin composition was prepared according to the same method as Example 1 except that 3.7 wt % of the dye was used instead of 5 wt % of the dye, "2.5 wt % of Pigment G58 pigment dispersion liquid and 13.7 wt % of Pigment Y138 pigment dispersion liquid" were used instead of "15.0 wt % of Pigment Y138 pigment dispersion liquid", and 30.1 wt % of PGMEA was used instead of 30.0 wt % of PGMEA.

Example 12

A photosensitive resin composition was prepared according to the same method as Example 11 except for using the compound of Synthesis Example 10 (represented by Chemical Formula 6) instead of the compound of Synthesis Example 9 (represented by Chemical Formula 5).

Example 13

A photosensitive resin composition was prepared according to the same method as Example 11 except for using the compound of Synthesis Example 11 (represented by Chemical Formula 7) instead of the compound of Synthesis Example 9 (represented by Chemical Formula 5).

Example 14

A photosensitive resin composition was prepared according to the same method as Example 11 except for using the compound of Synthesis Example 12 (represented by Chemical Formula 8) instead of the compound of Synthesis Example 9 (represented by Chemical Formula 5).

Example 15

A photosensitive resin composition was prepared according to the same method as Example 11 except for using the compound of Synthesis Example 13 (represented by Chemical Formula 9) instead of the compound of Synthesis Example 9 (represented by Chemical Formula 5).

Example 16

A photosensitive resin composition was prepared according to the same method as Example 11 except for using the compound of Synthesis Example 14 (represented by Chemical Formula 10) instead of the compound of Synthesis Example 9 (represented by Chemical Formula 5).

Example 17

A photosensitive resin composition was prepared according to the same method as Example 11 except for using the compound of Synthesis Example 15 (represented by Chemical Formula 11) instead of the compound of Synthesis Example 9 (represented by Chemical Formula 5).

Example 18

A photosensitive resin composition was prepared according to the same method as Example 11 except for using the compound of Synthesis Example 16 (represented by Chemical Formula 12) instead of the compound of Synthesis Example 9 (represented by Chemical Formula 5).

Example 19

A photosensitive resin composition was prepared according to the same method as Example 11 except for using the compound of Synthesis Example 17 (represented by Chemical Formula 13) instead of the compound of Synthesis Example 9 (represented by Chemical Formula 5).

Example 20

A photosensitive resin composition was prepared according to the same method as Example 11 except for using the compound of Synthesis Example 18 (represented by Chemical Formula 14) instead of the compound of Synthesis Example 9 (represented by Chemical Formula 5).

Comparative Example 1

A photosensitive resin composition was prepared according to the same method as Example 1 except for using the compound of Comparative Synthesis Example 1 (represented by Chemical Formula X) instead of the compound of Synthesis Example 9 (represented by Chemical Formula 5).

Comparative Example 2

A photosensitive resin composition was prepared according to the same method as Example 1 except for performing the mixing with the following compositions in Table 2 instead of the compositions in Table 1.

TABLE 2

| Formulation materials | | | Amount |
|---|---|---|---|
| Colorant | Pigment dispersion liquid | Pigment G58 pigment dispersion liquid | 20.0 |
| | | Pigment Y138 pigment dispersion liquid | 15.0 |
| Binder resin | | (A)/(B) = 15/85 (w/w), molecular weight (Mw) = 22,000 g/mol (A): methacrylic acid (B): benzylmethacrylate | 2.5 |
| Photopolymerizable compound | | Dipentaerythritolhexaacrylate (DPHA) | 5.0 |
| Photopolymerization initiator | | 1,2-octandione | 1.0 |
| | | 2-dimethylamino-2-(4-methylbenzyl)-1-(4-morpholin-4-yl-phenyl)-butan-1-one | 0.5 |
| Solvent | | Cyclohexanone | 40.0 |
| | | PGMEA (Propylene Glycol Monomethyl Ether Acetate) | 16.0 |
| Total | | | 100.00 |

(unit: wt %)

Evaluation 1: Evaluation of Luminance and Contrast Ratio

The photosensitive resin compositions according to Examples 1 to 20 and Comparative Examples 1 and 2 were respectively coated to be 1 μm to 3 μm thick on a 1 mm-thick defatted glass substrate, and then dried on a 90° C. hot plate for 2 minutes to obtain films. The films were exposed by using a high pressure mercury lamp having a main wavelength of 365 nm. Subsequently, the films were dried in a 200° C. forced convection drying furnace for 5 minutes to obtain samples. Luminance (Y) and contrast ratios of pixel layers were measured by using a spectrophotometer (MCPD3000, Otsuka Electronics Co., Ltd.), and the results are provided in Table 3.

TABLE 3

| | Luminance (Y) | Contrast ratio |
|---|---|---|
| Example 1 | 63.2 | 15,700 |
| Example 2 | 63.6 | 15,600 |
| Example 3 | 63.3 | 15,200 |
| Example 4 | 63.3 | 15,200 |
| Example 5 | 63.1 | 15,400 |
| Example 6 | 62.8 | 15,300 |
| Example 7 | 62.9 | 15,200 |
| Example 8 | 63.0 | 15,300 |
| Example 9 | 62.8 | 15,500 |
| Example 10 | 62.6 | 15,500 |
| Example 11 | 62.8 | 14,900 |
| Example 12 | 63.0 | 14,800 |
| Example 13 | 62.9 | 14,600 |
| Example 14 | 62.8 | 14,700 |
| Example 15 | 62.7 | 14,800 |
| Example 16 | 62.6 | 15,000 |
| Example 17 | 62.7 | 14,800 |
| Example 18 | 62.7 | 14,700 |
| Example 19 | 62.5 | 14,900 |
| Example 20 | 62.4 | 14,800 |
| Comparative Example 1 | 62.3 | 14,300 |
| Comparative Example 2 | 62.1 | 13,800 |

Referring to Table 3, the photosensitive resin compositions of Examples 1 to 20 including the compound according to one embodiment as a dye, specifically, the photosensitive resin compositions of Examples 1 to 9 showed excellent color characteristics compared with the photosensitive resin compositions of Comparative Examples 1 and 2.

By way of summation and review, a liquid crystal display device may include a lower substrate, on which a black matrix, a color filter, and an ITO pixel electrode are formed, and an upper substrate, on which an active circuit portion including a liquid crystal layer, a thin film transistor, and a capacitor layer and an ITO pixel electrode are formed.

Color filters may be formed in a pixel region by sequentially stacking a plurality of color filters (in general, formed of three primary colors such as red (R), green (G), and blue (B)) in a predetermined order to form each pixel, and a black matrix layer may be disposed in a predetermined pattern on a transparent substrate to form a boundary between the pixels. A pigment dispersion method may be used to form a color filter, by providing a colored thin film by repeating a series of processes such as coating a photopolymerizable composition including a colorant on a transparent substrate including a black matrix, exposing a formed pattern to light, removing a non-exposed part with a solvent, and thermally curing the same. A coloring photosensitive resin composition used for manufacturing a color filter by the pigment dispersion method may include an alkali soluble resin, a photopolymerization monomer, a photopolymerization initiator, an epoxy resin, a solvent, other additives, and the like. The pigment dispersion method may be applied to manufacture, for example, an LCD such as a mobile phone, a laptop, a monitor, and TV. High performance, excellent pattern profiles, high color reproducibility, and high luminance and high contrast ratio characteristics are important challenges for the pigment dispersion method.

A color filter manufactured by using a pigment-type photosensitive resin composition may be limited in luminance and a contrast ratio due to a pigment particle size. In addition, a color image sensor device for an image sensor may need a smaller dispersion particle diameter to form a fine pattern.

Consideration has been given to forming a color filter having improved luminance and a contrast ratio by introducing a dye forming no particle, instead of or in addition to the pigment, to prepare a photosensitive resin composition using the dye.

As described above, the compound represented by Chemical Formula 1 may provide excellent green spectral characteristics, a high molar extinction coefficient, and excellent solubility in an organic solvent, and thus may be used as a dye for a green photosensitive resin composition for a color filter, and accordingly, a color filter including the dye may have excellent color strength, transmittance, luminance, and contrast ratio.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound represented by Chemical Formula 1:

[Chemical Formula 1]

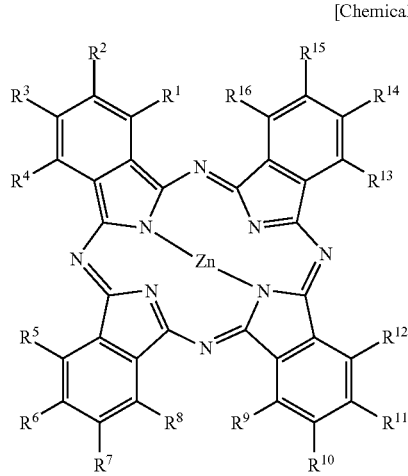

wherein, in Chemical Formula 1, $R^1$ to $R^{16}$ are independently a hydrogen atom, a halogen atom, a substituted or unsubstituted C1 to C20 alkyl group, a substituted or unsubstituted C3 to C20 alkoxy group, a substituted or unsubstituted C6 to C20 aryl group, or a substituted or unsubstituted C6 to C20 aryloxy group, provided that:
at least one of $R^1$ to $R^{16}$ is represented by Chemical Formula 2, and
at least one of $R^1$ to $R^{16}$ is represented by Chemical Formula 4,

[Chemical Formula 2]

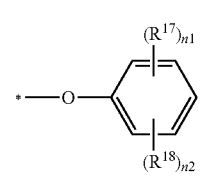

wherein in Chemical Formula 2,
$R^{17}$ and $R^{18}$ are independently a halogen atom, and
n1 and n2 are independently an integer ranging from 0 to 5, provided that $1 \leq n1+n2 \leq 5$,

[Chemical Formula 4]

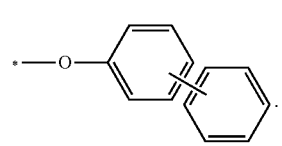

2. The compound as claimed in claim 1, wherein Chemical Formula 2 is represented by one selected from Chemical Formula 3-1 to Chemical Formula 3-4:

[Chemical Formula 3-1]

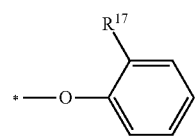

[Chemical Formula 3-2]

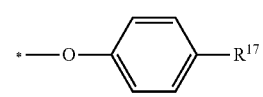

[Chemical Formula 3-3]

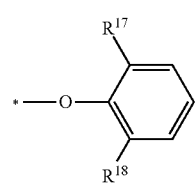

[Chemical Formula 3-4]

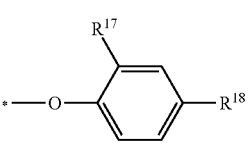

wherein in Chemical Formulae 3-1 to 3-4,
$R^{17}$ and $R^{18}$ are independently a halogen atom.

3. The compound as claimed in claim 1, wherein:
at least one of $R^1$ to $R^4$ is represented by Chemical Formula 2,
at least one of $R^5$ to $R^8$ is represented by Chemical Formula 4,
at least one of $R^9$ to $R^{12}$ is represented by Chemical Formula 4, and
at least one of $R^{13}$ to $R^{16}$ is represented by Chemical Formula 4.

4. The compound as claimed in claim 1, wherein:
at least one of $R^1$ to $R^4$ is represented by Chemical Formula 2,
at least one of $R^5$ to $R^8$ is represented by Chemical Formula 2,
at least one of $R^9$ to $R^{12}$ is represented by Chemical Formula 4, and
at least one of the $R^{13}$ to $R^{16}$ is represented by Chemical Formula 4.

5. The compound as claimed in claim 1, wherein:
at least one of $R^1$ to $R^4$ is represented by Chemical Formula 2,
at least one of $R^5$ to $R^8$ is represented by Chemical Formula 4,
at least one of $R^9$ to $R^{12}$ is represented by Chemical Formula 2, and
at least one of $R^{13}$ to $R^{16}$ is represented by Chemical Formula 4.

6. The compound as claimed in claim 1, wherein:
at least one of $R^1$ to $R^4$ is represented by Chemical Formula 2,
at least one of $R^5$ to $R^8$ is represented by Chemical Formula 2,
at least one of $R^9$ to $R^{12}$ is represented by Chemical Formula 2, and
at least one of $R^{13}$ to $R^{16}$ is represented by Chemical Formula 4.

7. The compound as claimed in claim 1, wherein the compound represented by Chemical Formula 1 is represented by one of the following Chemical Formulae:

[Chemical Formula 5]

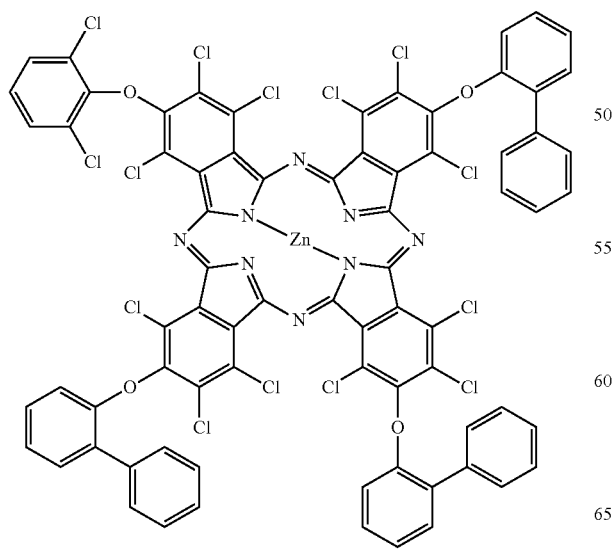

[Chemical Formula 6]

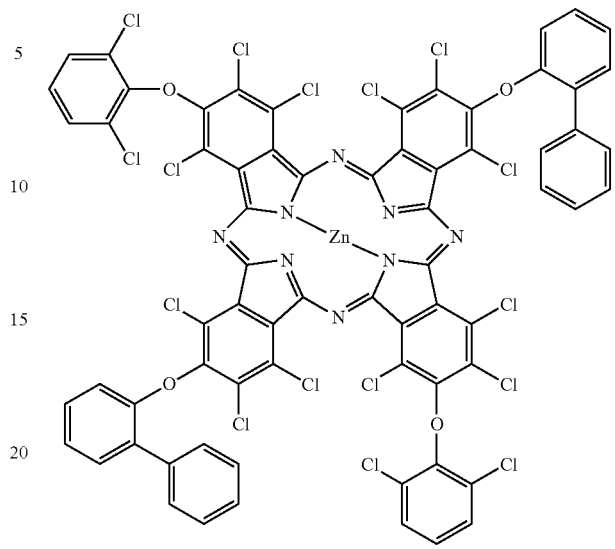

[Chemical Formula 7]

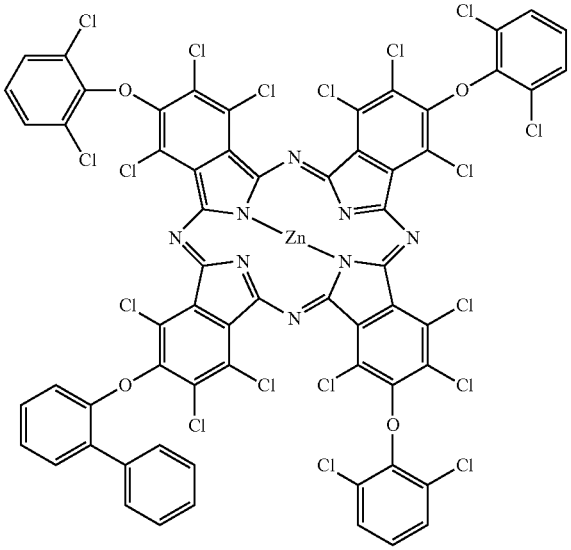

-continued

[Chemical Formula 14]

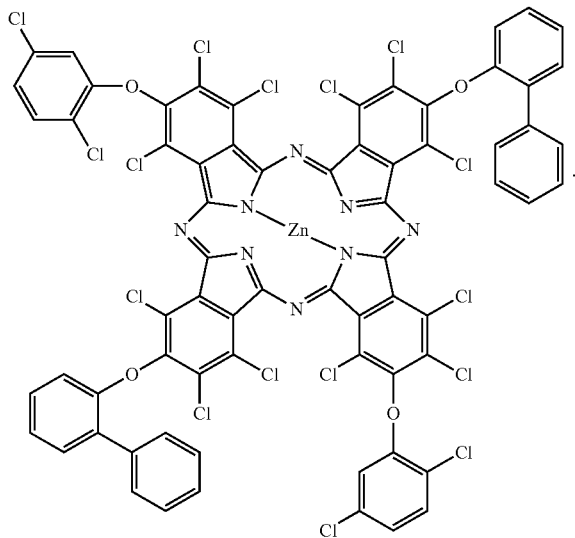

8. The compound as claimed in claim 1, wherein the compound is a green dye.

9. The compound as claimed in claim 8, wherein the green dye has maximum transmittance in a 445 nm to 560 nm wavelength range.

10. A photosensitive resin composition comprising the compound as claimed in claim 1.

11. The photosensitive resin composition as claimed in claim 10, wherein the photosensitive resin composition includes about 1 wt % to about 10 wt % of the compound based on a total amount of the photosensitive resin composition.

12. The photosensitive resin composition as claimed in claim 10, wherein the photosensitive resin composition further includes a binder resin, a photopolymerizable compound, a photopolymerization initiator, and a solvent.

13. The photosensitive resin composition as claimed in claim 10, wherein the photosensitive resin composition further includes a pigment.

14. The photosensitive resin composition as claimed in claim 13, wherein the pigment includes a yellow pigment, a green pigment, or a combination thereof.

15. A color filter manufactured using the photosensitive resin composition as claimed in claim 10.

16. A color filter comprising the compound as claimed in claim 1.

17. An electronic device comprising a display having a color filter, the color filter including the compound as claimed in claim 1.

* * * * *